US012565503B2

(12) United States Patent

Dai et al.

(10) Patent No.: US 12,565,503 B2

(45) Date of Patent: Mar. 3, 2026

(54) CYCLIC GD (III) COMPLEX AND PREPARATION METHOD AND USE THEREOF

(71) Applicant: Wenzhou Institute, University of Chinese Academy of Sciences, Zhejiang (CN)

(72) Inventors: Lixiong Dai, Zhejiang (CN); Weiyuan Xu, Zhejiang (CN); Fangfu Ye, Zhejiang (CN)

(73) Assignee: Wenzhou Institute, University of Chinese Academy of Sciences, Zhejiang (CN)

( * ) Notice: Subject to any disclaimer, the term of this patent is extended or adjusted under 35 U.S.C. 154(b) by 598 days.

(21) Appl. No.: 17/997,450

(22) PCT Filed: Jun. 23, 2022

(86) PCT No.: PCT/CN2022/100671

§ 371 (c)(1),
(2) Date: Oct. 28, 2022

(87) PCT Pub. No.: WO2023/173618

PCT Pub. Date: Sep. 21, 2023

(65) Prior Publication Data

US 2025/0154159 A1 May 15, 2025

(30) Foreign Application Priority Data

Mar. 16, 2022 (CN) ......................... 202210256593.2

(51) Int. Cl.
*C07D 487/22* (2006.01)

(52) U.S. Cl.
CPC .................................. *C07D 487/22* (2013.01)

(58) Field of Classification Search
None
See application file for complete search history.

(56) References Cited

PUBLICATIONS

AIME (Relaxometric, Structural, and Dynamic NMR Studies of DOTA-like Ln(III) Complexes (Ln=La, Gd, Ho, Yb) Containing a p-Nitrophenyl Substituent. Inorganic Chemistry. 1996.) (Year: 1996).*

* cited by examiner

*Primary Examiner* — Michael G. Hartley
*Assistant Examiner* — Samantha L Mejias
(74) *Attorney, Agent, or Firm* — SALIWANCHIK, LLOYD & EISENSCHENK

(57) ABSTRACT

The present disclosure provides a cyclic Gd (III) complex with a chemical structure shown in formula I, where a ring structure of 1,4,7,10-tetraazacyclododecane-1,4,7,10-tetraacetic acid (DOTA) is used as a parent ring, lipophilic groups R' and R" in formula I are respectively introduced to a α-position of phenylacetic acid (PAA) and a benzene ring structure, and a chiral group R in formula I is introduced to a DOTA macrocycle position. The chiral group R can increase the rigidity of a macrocyclic structure and improve the stability of the complex, and the lipophilic groups R' and R" can bind to hepatocellular organic anion transporting polypeptides (OATPs), thereby greatly improving the distribution of the cyclic Gd (III) complex as a contrast agent in the liver and gallbladder, that is, thereby providing excellent targetability.

15 Claims, 2 Drawing Sheets

CYCLIC GD (III) COMPLEX AND PREPARATION METHOD AND USE THEREOF

CROSS REFERENCE TO RELATED APPLICATIONS

This application is the U.S. national stage application of International Patent Application No. PCT/CN2022/100671, filed Jun. 23, 2022, which claims the benefit under 35 U.S.C. § 119 of Chinese Application No. 202210256593.2, filed Mar. 16, 2022, the disclosures of each of which are incorporated herein by reference in their entirety.

TECHNICAL FIELD

The present disclosure relates to the technical field of organic complexes, and in particular to a cyclic Gd (III) complex and a preparation method and use thereof.

BACKGROUND

Magnetic resonance imaging (MRI) is a technology in which an electromagnetic signal (EMS) is acquired through magnetic resonance of atomic nuclei under the action of a magnetic field and imaging is conducted with the help of computer technology and image reconstruction. The MRI technology neither relies on external radiation, absorption, and reflection, nor emits γ rays, which is harmless to the human body. Moreover, MRI exhibits a unique advantage for the detection of liver cancer, that is, MRI can provide multi-parameter, multi-directional, and high-soft-tissue-contrast imaging. However, MRI shows relatively-low detection sensitivity. About 40% of MRI detection requires the use of a contrast agent to improve a detection signal, and about 60% of MRI detection for a nervous system requires the use of a contrast agent. About 40 million people require the use of an MRI contrast agent every year worldwide.

The current commercial hepatobiliary MRI contrast agents are mostly linear Gd-DTPA derivatives, such as Gd-EOB-DTPA (commercial names: Primovist, Eovist, and Primovist). However, the above-mentioned commercial Gd-based MRI contrast agents have disadvantages such as large Gd residue caused by poor stability and poor targetability, which pose high health risks. Therefore, how to provide a hepatobiliary-targeted MRI contrast agent with excellent stability is an urgent problem to be solved in the prior art.

SUMMARY

The present disclosure is intended to provide a cyclic Gd (III) complex and a preparation method and use thereof. The cyclic Gd (III) complex provided by the present disclosure can be used as an MRI contrast agent targeting the liver and gallbladder, with excellent stability and targetability.

To achieve the above purpose, the present disclosure provides the following technical solutions.

The present disclosure provides a cyclic Gd (III) complex with a chemical structure shown in formula I:

formula I

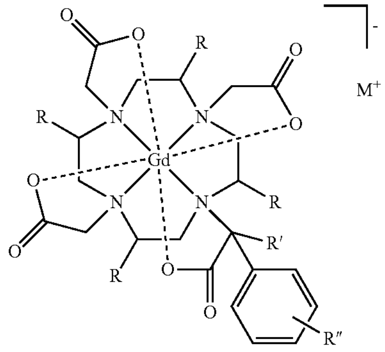

, where R in formula I is selected from the group consisting of H, $C_1$-$C_4$ alkyl, $-CH_2OH$, $-CH(CH_3)OH$, $-CH_2CH_2OH$, $-CH_2Ph$, $-(CH_2)_2Ph$, $-(CH_2)_3Ph$, $-(CH_2)_3NH_2$, and $-(CH_2)_4Ph$, and R in formula I has a configuration independently of S or R;

R" in formula I is at an ortho, meta, or para position of a benzene ring;

R' and R" in formula I are each independently selected from the group consisting of H, $C_1$-$C_{10}$ alkyl, fluorine, chlorine, bromine, iodine, $-CF_3$, $-CCl_3$, $-CBr_3$, $C_1$-$C_{10}$ alkoxy, $-COOH$, $-R_1COOH$, $-COOR_1$, -Ph, $-NO_2$, substituted phenyl, $-R_1$-Ph, $-R_1NO_2$, $-OR_1$-Ph, $-CONHR_3$,

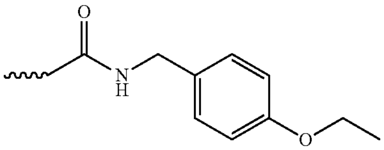

,

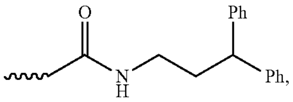

, $SO_2-R_4$, and $-SO-R_5$;

$R_1$ in each of $-R_1COOH$, $-COOR_1$, $-R_1$-Ph, $-R_1NO_2$, and $-OR_1$-Ph is independently $C_1$-$C_5$ alkyl;

a substituent on the substituted phenyl is selected from the group consisting of $C_1$-$C_5$ alkyl, fluorine, chlorine, bromine, iodine, $-CF_3$, $-CCl_3$, $-CBr_3$, $C_1$-$C_5$ alkoxy, $-COOH$, $-R_2COOH$, $-COOR_2$, -Ph, $-R_2NO_2$, $-OR_2$-Ph, $-CONHR_2$, $-SO_2-R_2$, and $-SO-R_2$, and $R_2$ in each of $-R_2COOH$, $-COOR_2$, -Ph, $-R_2NO_2$, $-OR_2$-Ph, $-CONHR_2$, $-SO_2-R_2$, and $-SO-R_2$ is independently $C_1$-$C_3$ alkyl;

$R_3$, $R_4$, and $R_5$ respectively in $-CONHR_3$, $-SO_2$-$R_4$, and $-SO-R_5$ are each independently $C_1$-$C_5$ alkyl or benzyl; and $M^+$ in formula I is a metal cation or a glucosamine cation.

Preferably, R in formula I is selected from the group consisting of H, $-CH_3$, $-CH_2CH_3$, $-CH(CH_3)_2$, $-CH(CH_3)OH$, $-CH_2Ph$, and $-(CH_2)_4Ph$;

R' and R" in formula I are each independently selected from the group consisting of H, $-COOH$, $CONHR_3$, $-CF_3$, $-C(CH_3)_3$, -Ph, $-NO_2$, $-OBn$,

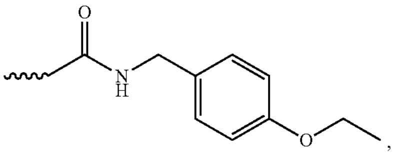

,

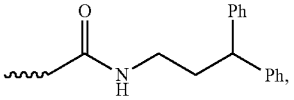

$SO_2$—$R_4$, and —SO—$R_5$; and $R_3$, $R_4$, and $R_5$ respectively in —$CONHR_3$, —$SO_2$-$R_4$, and —SO—$R_5$ are each independently $C_1$-$C_5$ alkyl or benzyl.

Preferably, $M^+$ in formula I is selected from the group consisting of $Na^+$, $K^+$, $Li^+$, and a glucosamine cation.

The present disclosure further provides a preparation method of the above-described cyclic Gd (III) complex, where in formula I, R is H, R' is H, and R" is

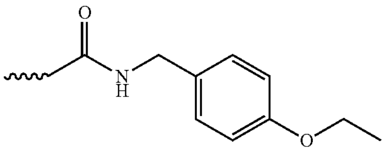

or

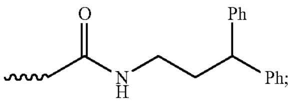

;

and the preparation method includes the following steps:

(1) in a nitrogen atmosphere, mixing a compound with a structure shown in formula A-1, DO3A, potassium carbonate, and acetonitrile to allow a nucleophilic substitution reaction to obtain a compound with a structure shown in formula A-2;

(2) mixing the compound with a structure shown in formula A-2 obtained in step (1), tetrahydrofuran (THF), methanol, and a lithium hydroxide aqueous solution to allow a hydrolysis reaction to obtain a first reaction precursor;

(3) in a nitrogen atmosphere, mixing the first reaction precursor obtained in step (2) with 2-(7-azabenzotriazol-1-yl)-N,N,N',N'-tetramethyluronium hexafluorophosphate (HATU), dichloromethane (DCM), an amine, and diisopropylethylamine (DIPEA) to allow a condensation reaction to obtain a compound with a structure shown in formula A-3;

(4) mixing the compound with a structure shown in formula A-3 obtained in step (3) and trifluoroacetic acid (TFA) to allow a t-butyl ester group removal reaction to obtain a compound with a structure shown in formula A-4; and (5) mixing the compound with a structure shown in formula A-4 obtained in step (4), a gadolinium source, water, and an $M^+$-containing solution to allow a complexation reaction to obtain the cyclic Gd (III) complex, where the $M^+$-containing solution in step (5) is a solution of a metal hydroxide or a glucosamine,

A-1

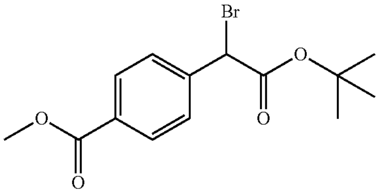

A-2

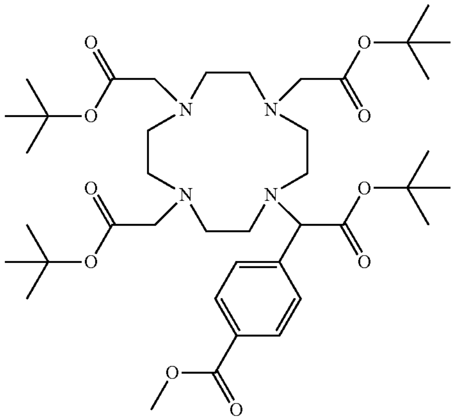

A-3

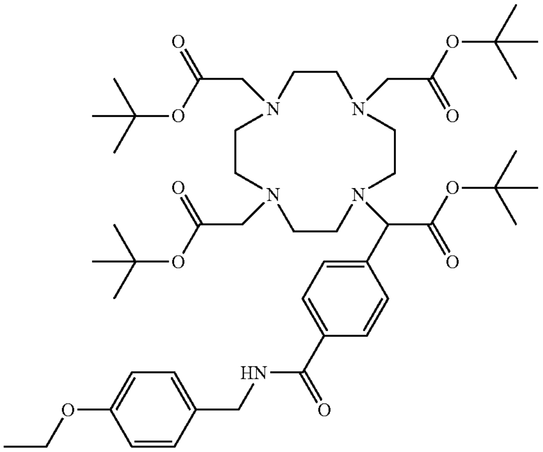

A-4

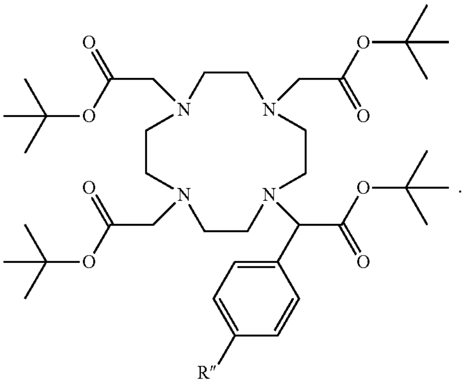

Preferably, the t-butyl ester group removal reaction in step (4) is conducted at room temperature for 10 h to 15 h.

The present disclosure further provides a preparation method of the above-described cyclic Gd (III) complex, where in formula I, R is H, R' is H, and R" is selected from the group consisting of H, —COOH, —$CF_3$, —$C(CH_3)_3$, -Ph, —$NO_2$, and —OBn; and the preparation method includes the following steps:

S1. in a nitrogen atmosphere, mixing a compound with a structure shown in formula B-1, acetonitrile, DO3A, and potassium carbonate to allow a nucleophilic substitution reaction to obtain a second reaction precursor;

S2. mixing the second reaction precursor obtained in S1 with hydrochloric acid to allow a t-butyl ester group removal reaction to obtain a compound with a structure shown in formula B-2; and S3. mixing the compound with a structure shown in formula B-2 obtained in S2, a gadolinium source, water, and an $M^+$-containing solution to allow a complexation reaction to obtain the cyclic Gd (III) complex, where the $M^+$-containing solution in S3 is a solution of a metal hydroxide or a glucosamine,

B-1

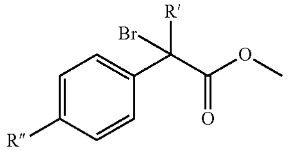

B-2

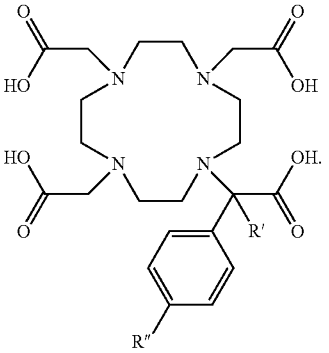

Preferably, the complexation reaction in S3 is conducted at 90° C. to 110° C. for 5 h to 7 h.

The present disclosure further provides a preparation method of the above-described cyclic Gd (III) complex, where in formula I, R is selected from the group consisting of $C_1$-$C_4$ alkyl, —$CH_2OH$, —$CH(CH_3)OH$, —$CH_2CH_2OH$, —$CH_2Ph$, —$(CH_2)_2Ph$, —$(CH_2)_3Ph$, —$(CH_2)_3NH_2$, and —$(CH_2)_4Ph$, R' is H, and R" is —COOH; and the preparation method includes the following steps:

(a) mixing a compound with a structure shown in formula C-1, a compound with a structure shown in chiral cyclen, and acetonitrile to allow a first nucleophilic substitution reaction to obtain a compound with a structure shown in formula C-2;

(b) in a nitrogen atmosphere, mixing the compound with a structure shown in formula C-2 obtained in step (a), acetonitrile, potassium carbonate, and tert-butyl bromoacetate to allow a second nucleophilic substitution reaction to obtain a compound with a structure shown in formula C-3;

(c) mixing the compound with a structure shown in formula C-3 obtained in step (b), THF, methanol, and a lithium hydroxide aqueous solution to allow a hydrolysis reaction to obtain a compound with a structure shown in formula C-4; and (d) mixing the compound with a structure shown in formula C-4 obtained in step (c), a gadolinium source, water, and an $M^+$-containing solution to allow a complexation reaction to obtain the cyclic Gd (III) complex, where the $M^+$-containing solution in step (d) is a solution of a metal hydroxide or a glucosamine,

C-1

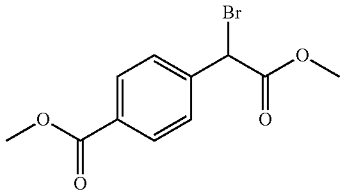

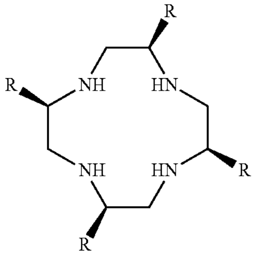

Chiral cyclen

C-2

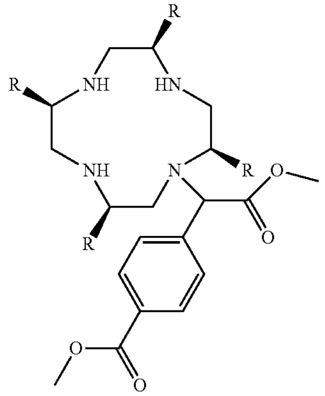

C-3

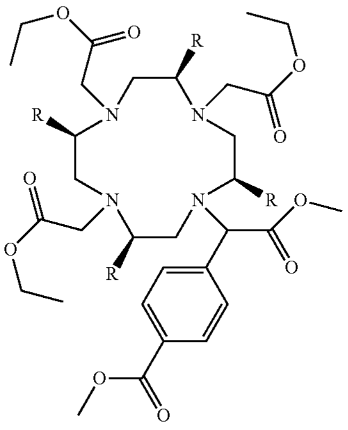

-continued

C-4

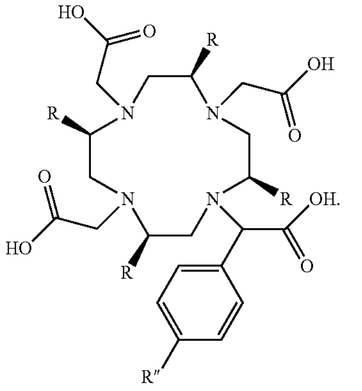

Preferably, in step (b), the second nucleophilic substitution reaction is conducted at room temperature for 16 h to 20 h.

The present disclosure further provides a preparation method of the above-described cyclic Gd (III) complex, where in formula I, R is selected from the group consisting of $C_1$-$C_4$ alkyl, —$CH_2OH$, —$CH(CH_3)OH$, —$CH_2CH_2OH$, —$CH_2Ph$, —$(CH_2)_2Ph$, —$(CH_2)_3Ph$, —$(CH_2)_3NH_2$, and —$(CH_2)_4Ph$, R' is H, and R" is

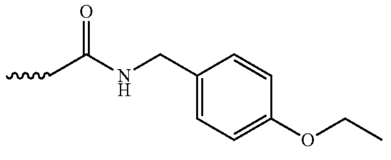

or

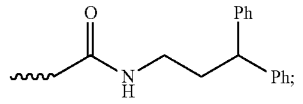

and the preparation method includes the following steps:

1) mixing a compound with a structure shown in formula A-1, a compound with a structure shown in chiral cyclen, and acetonitrile to allow a first nucleophilic substitution reaction to obtain a compound with a structure shown in formula D-2;
2) in a nitrogen atmosphere, mixing the compound with a structure shown in formula D-2 obtained in step 1), acetonitrile, potassium carbonate, and tert-butyl bromoacetate to allow a second nucleophilic substitution reaction to obtain a compound with a structure shown in formula D-3;
3) mixing the compound with a structure shown in formula D-3 obtained in step 2), THF, methanol, and a lithium hydroxide aqueous solution to allow an ester hydrolysis reaction to obtain a third reaction precursor;
4) in a nitrogen atmosphere, mixing the third reaction precursor obtained in step 3) with HATU, DCM, an amine compound, and DIPEA to allow a condensation reaction to obtain a compound with a structure shown in formula D-4;
5) in a nitrogen atmosphere, mixing the compound with a structure shown in formula D-4 obtained in step 4) and TFA to allow a t-butyl ester group removal reaction to obtain a compound with a structure shown in formula D-5; and 6) mixing the compound with a structure shown in formula D-5 obtained in step 5), a gadolinium source, water, and an $M^+$-containing solution to allow a complexation reaction to obtain the cyclic Gd (III) complex, where the $M^+$-containing solution in step 6) is a solution of a metal hydroxide or a glucosamine,

A-1

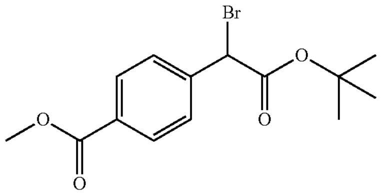

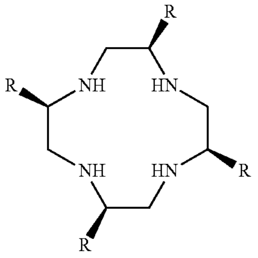

Chiral cyclen

D-2

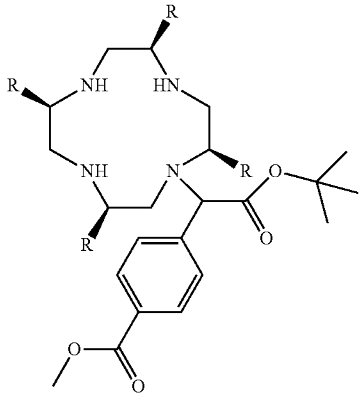

D-3

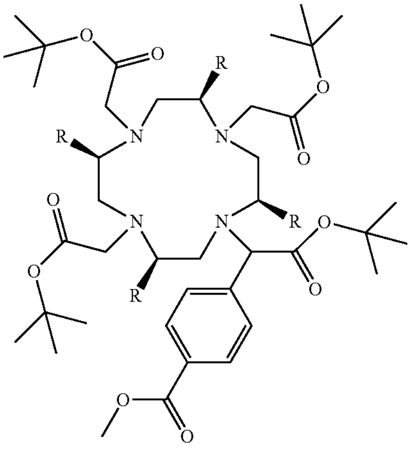

-continued

D-4

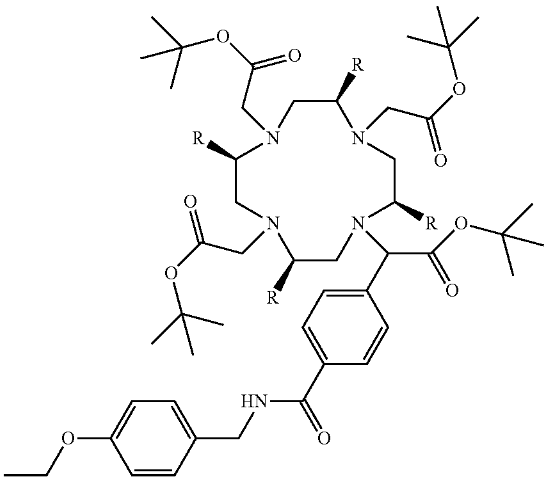

D-5

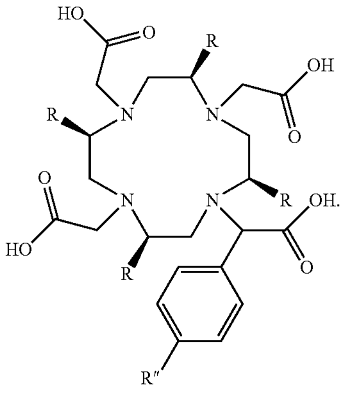

Preferably, the ester hydrolysis reaction in step 3) is conducted at room temperature for 4 h to 8 h.

The present disclosure further provides a preparation method of the above-described cyclic Gd (III) complex, where in formula I, R is selected from the group consisting of $C_1$-$C_4$ alkyl, —$CH_2OH$, —$CH(CH_3)OH$, —$CH_2CH_2OH$, —$CH_2Ph$, —$(CH_2)_2Ph$, —$(CH_2)_3Ph$, —$(CH_2)_3NH_2$, and —$(CH_2)_4Ph$, R' is H, and R" is selected from the group consisting of H, —$CF_3$, —$C(CH_3)_3$, -Ph, —$NO_2$, and —OBn; and the preparation method includes the following steps:

(1') in a nitrogen atmosphere, mixing a compound with a structure shown in formula E-1, a compound with a structure shown in chiral cyclen, and acetonitrile to allow a first nucleophilic substitution reaction to obtain a compound with a structure shown in formula E-2;

(2') in a nitrogen atmosphere, mixing the compound with a structure shown in formula E-2 obtained in step (1'), acetonitrile, potassium carbonate, and ethyl bromoacetate to allow a second nucleophilic substitution reaction to obtain a compound with a structure shown in formula E-3;

(3') mixing the compound with a structure shown in formula E-3 obtained in step (2'), THF, methanol, and a lithium hydroxide aqueous solution to allow an ester hydrolysis reaction, and subjecting a product of the ester hydrolysis reaction to concentration, dilution, and pH adjustment successively to obtain a compound with a structure shown in formula E-4; and (4') mixing the compound with a structure shown in formula E-4 obtained in step (3'), a gadolinium source, water, and an $M^+$-containing solution to allow a complexation reaction to obtain the cyclic Gd (III) complex, where the $M^+$-containing solution in step (4') is a solution of a metal hydroxide or a glucosamine,

E-1

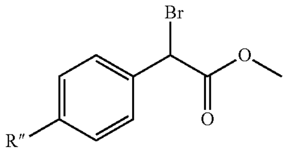

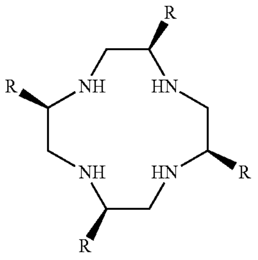

Chiral cyclen

E-2

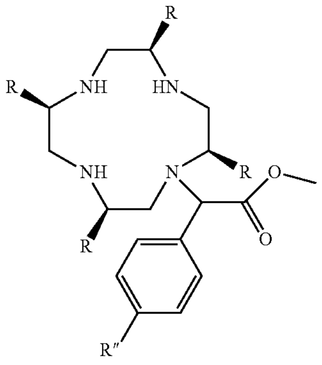

E-3

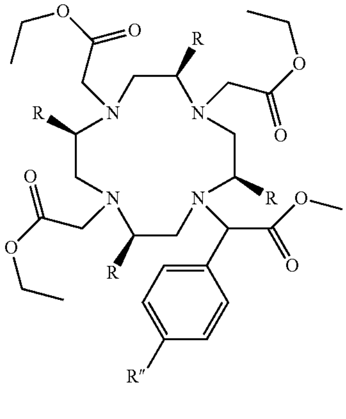

-continued

E-4

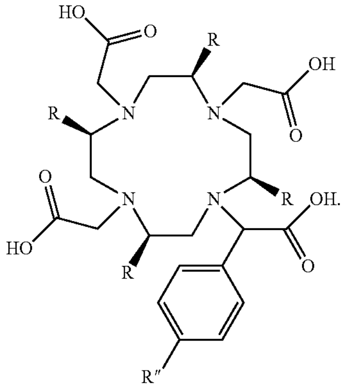

Preferably, the complexation reaction in step (4') is conducted at 90° C. to 110° C. for 5 h to 7 h.

The present disclosure further provides a pharmaceutical composition including the above-described cyclic Gd (III) complex.

The present disclosure further provides use of the above-described cyclic Gd (III) complex or the above-described pharmaceutical composition in magnetic resonance imaging (MRI).

The present disclosure provides a cyclic Gd (III) complex with a chemical structure shown in formula I, where a ring structure of 1,4,7,10-tetraazacyclododecane-1,4,7,10-tetraacetic acid (DOTA) is used as a parent ring, lipophilic groups R' and R" in formula I are respectively introduced to a α-position of phenylacetic acid (PAA) and a benzene ring structure, and a chiral group R in formula I is introduced to a DOTA macrocycle position. The chiral group R can increase the rigidity of a macrocyclic structure and improve the stability of the complex, and the lipophilic groups R' and R" can bind to hepatocellular organic anion transporting polypeptides (OATPs), thereby greatly improving the distribution of the cyclic Gd (III) complex as a contrast agent in the liver and gallbladder, that is, thereby providing excellent targetability. The results of examples show that the cyclic Gd (III) complex provided by the present disclosure exhibits excellent targetability to the liver and gallbladder and has the optimal relaxation rate range for MRI, where GdL9 has a relaxation rate suitable for high-field MRI; the cyclic Gd (III) complex has high stability, which is significantly higher than that of Primovist and Gd-DOTA; and after the chiral group R is introduced, the stability of the cyclic Gd (III) complex is greatly improved, where the release of metal ions is not detected in GdL9 and GdL10 within 1 year, indicating excellent stability. Therefore, the cyclic Gd (III) complex can be used as a liver and gallbladder-specific MRI contrast agent.

DETAILED DESCRIPTION OF THE EMBODIMENTS

Figure 1:
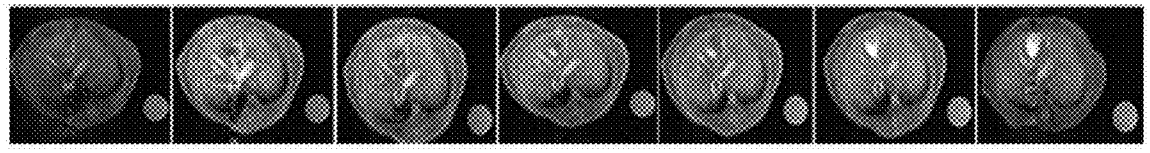
FIG. 1 shows hepatobiliary MRI images obtained when the complex GdL1 prepared in Example 1 of the present disclosure is used as a liver and gallbladder-targeted MRI contrast agent to detect the liver and gallbladder of mice at 0 min, 5 min, 10 min, 20 min, 30 min, 1 h, and 2 h after the mice are administered with GdL1.

The present disclosure provides a cyclic Gd (III) complex with a chemical structure shown in formula I:

formula I

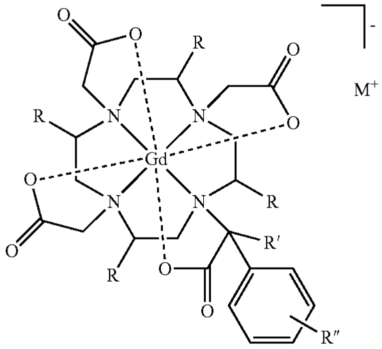

, where R in formula I is selected from the group consisting of H, $C_1$-$C_4$ alkyl, —$CH_2OH$, —$CH(CH_3)OH$, —$CH_2CH_2OH$, —$CH_2Ph$, —$(CH_2)_2Ph$, —$(CH_2)_3Ph$, —$(CH_2)_3NH_2$, and —$(CH_2)_4Ph$ and preferably selected from the group consisting of H, —$CH_3$, —$CH_2CH_3$, —$CH(CH_3)_2$, —$CH(CH_3)OH$, —$CH_2Ph$, and —$(CH_2)_4Ph$, and R in formula I has a configuration independently of S or R;

R" in formula I is at an ortho, meta, or para position of a benzene ring;

R' and R' in formula I are each independently selected from the group consisting of H, $C_1$-$C_{10}$ alkyl, fluorine, chlorine, bromine, iodine, —$CF_3$, —$CCl_3$, —$CBr_3$, $C_1$-$C_{10}$ alkoxy, —COOH, —$R_1$COOH, —$COOR_1$, -Ph, substituted phenyl, —$R_1$-Ph, —$R_1NO_2$, —$OR_1$-Ph, —$CONHR_3$,

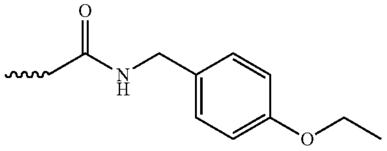
,
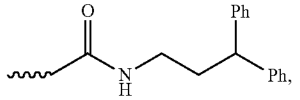
,

—$SO_2$—$R_4$, and —SO—$R_5$, preferably selected from the group consisting of H, —COOH, $CONHR_3$, —$CF_3$, —$C(CH_3)_3$, -Ph, —$NO_2$, —OBn,

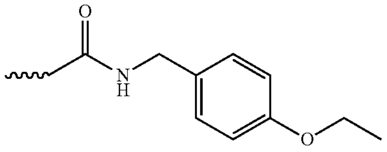
,
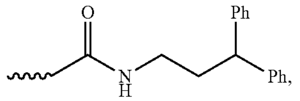
,

—$SO_2$—$R_4$, and —SO—$R_5$, and more preferably selected from the group consisting of H, —COOH, —$CF_3$, —$C(CH_3)_3$, -Ph, —$NO_2$, —OBn,

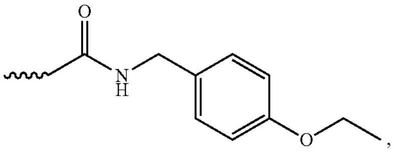
, and
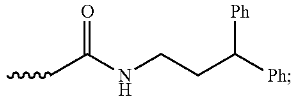
;

- $R_1$ in each of —$R_1$COOH, —$COOR_1$, —$R_1$-Ph, —$R_1NO_2$, and —$OR_1$-Ph is independently $C_1$-$C_5$ alkyl;
- a substituent on the substituted phenyl is selected from the group consisting of $C_1$-$C_5$ alkyl, fluorine, chlorine, bromine, iodine, —$CF_3$, —$CCl_3$, —$CBr_3$, $C_1$-$C_5$ alkoxy, —COOH, —$R_2$COOH, —$COOR_2$, -Ph, —$R_2NO_2$, —$OR_2$-Ph, —$CONHR_2$, —$SO_2$—$R_2$, and —SO—$R_2$, and $R_2$ in each of —$R_2$COOH, —$COOR_2$, -Ph, —$R_2NO_2$, —$OR_2$-Ph, —$CONHR_2$, —$SO_2$—$R_2$, and —SO—$R_2$ is independently $C_1$-$C_3$ alkyl;
- $R_3$, $R_4$, and $R_5$ respectively in —$CONHR_3$, —$SO_2$-$R_4$, and —SO—$R_5$ are each independently $C_1$-$C_5$ alkyl or benzyl;
- R' in formula I is more preferably selected from the group consisting of H, —COOH, —$CF_3$, —$C(CH_3)_3$, and -Ph; and
- $M^+$ in formula I is a metal cation or a glucosamine cation, and is preferably selected from the group consisting of $Na^+$, $K^+$, $Li^+$, and a glucosamine cation.

In the present disclosure, the cyclic Gd (III) complex with a chemical structure shown in formula I is preferably any one selected from the group consisting of GdL1

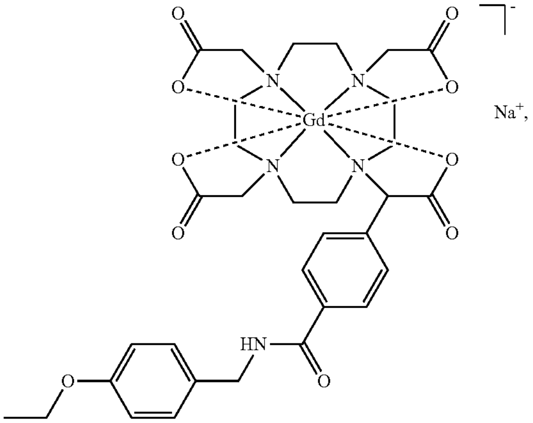
,

GdL2

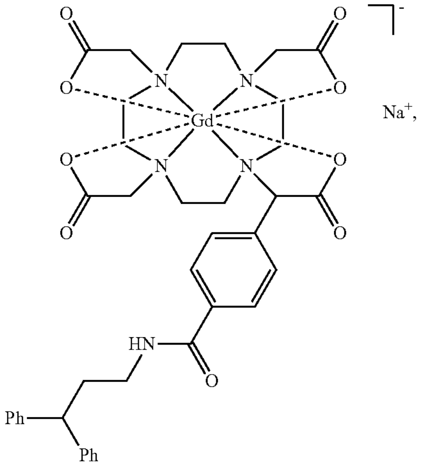
,

GdL3

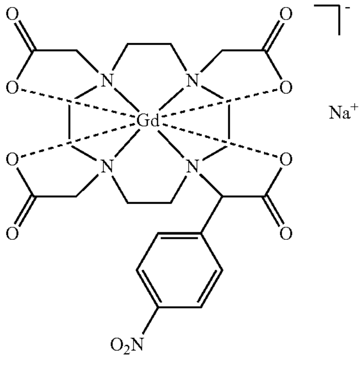

GdL4

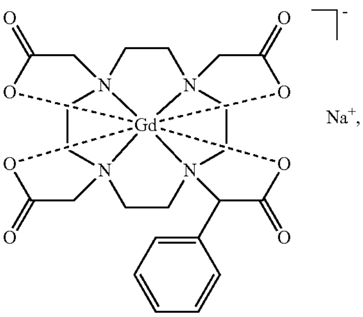
,

-continued
GdL5
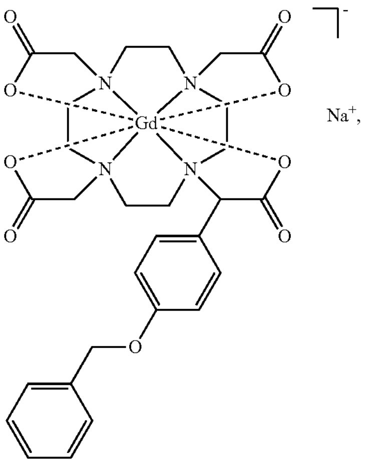
GdL6
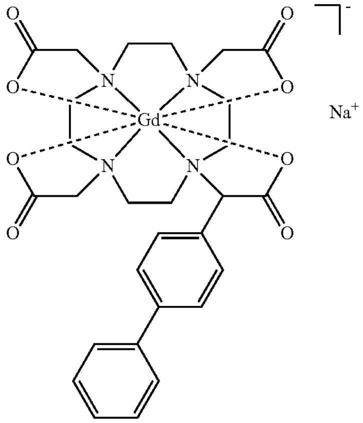
GdL7
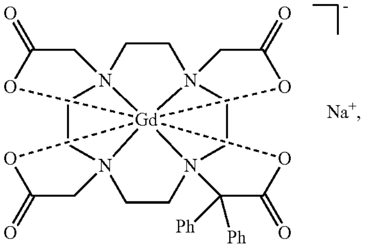
GdL8
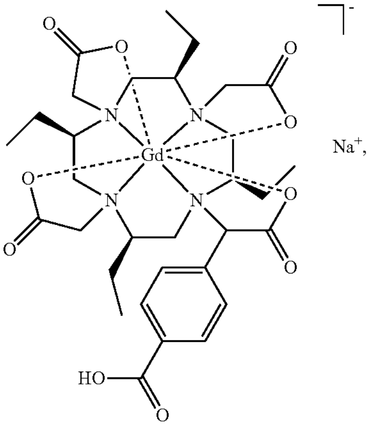
-continued
GdL9
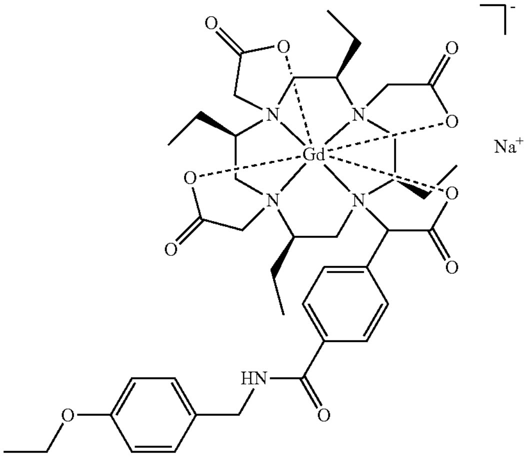
GdL10
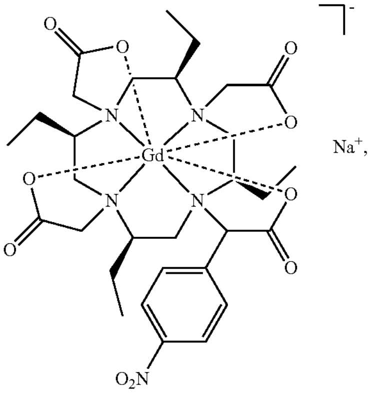
GdL11
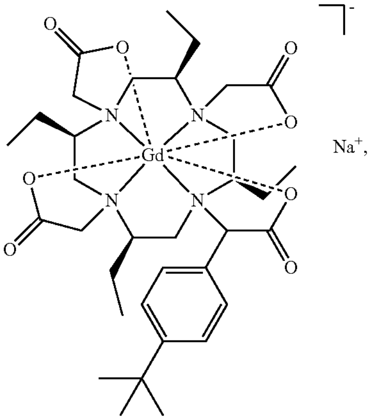

-continued

GdL12

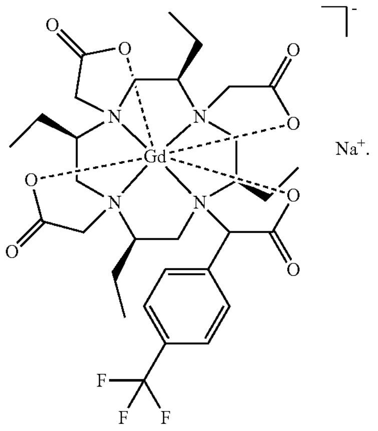

The cyclic Gd (III) complex provided by the present disclosure can be used as an MRI contrast agent targeting the liver and gallbladder, with excellent stability and targetability.

The present disclosure also provides a preparation method of the cyclic Gd (III) complex described in the above technical solution.

In the present disclosure, when R is H, R' is H, and R" is

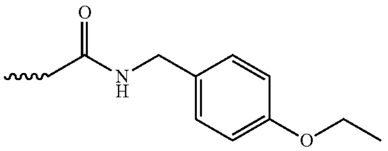

or

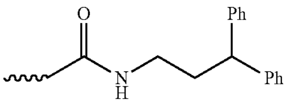

in formula I, the preparation method of the cyclic Gd (III) complex includes the following steps:

(1) in a nitrogen atmosphere, mixing a compound with a structure shown in formula A-1, DO3A, potassium carbonate, and acetonitrile to allow a nucleophilic substitution reaction to obtain a compound with a structure shown in formula A-2;

(2) mixing the compound with a structure shown in formula A-2 obtained in step (1), tetrahydrofuran (THF), methanol, and a lithium hydroxide aqueous solution to allow a hydrolysis reaction to obtain a first reaction precursor;

(3) in a nitrogen atmosphere, mixing the first reaction precursor obtained in step (2) with 2-(7-azabenzotriazol-1-yl)-N,N,N',N'-tetramethyluronium hexafluorophosphate (HATU), dichloromethane (DCM), an amine, and diisopropylethylamine (DIPEA) to allow a condensation reaction to obtain a compound with a structure shown in formula A-3;

(4) mixing the compound with a structure shown in formula A-3 obtained in step (3) and trifluoroacetic acid (TFA) to allow a t-butyl ester group removal reaction to obtain a compound with a structure shown in formula A-4; and (5) mixing the compound with a structure shown in formula A-4 obtained in step (4), a gadolinium source, water, and an $M^+$-containing solution to allow a complexation reaction to obtain the cyclic Gd (III) complex, where the $M^+$-containing solution in step (5) is a solution of a metal hydroxide or a glucosamine.

A-1

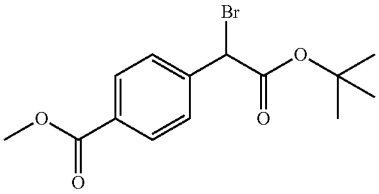

A-2

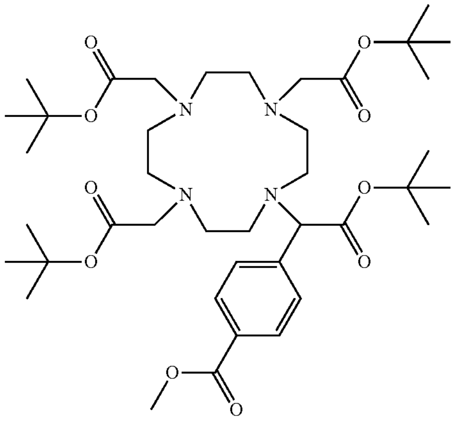

A-3

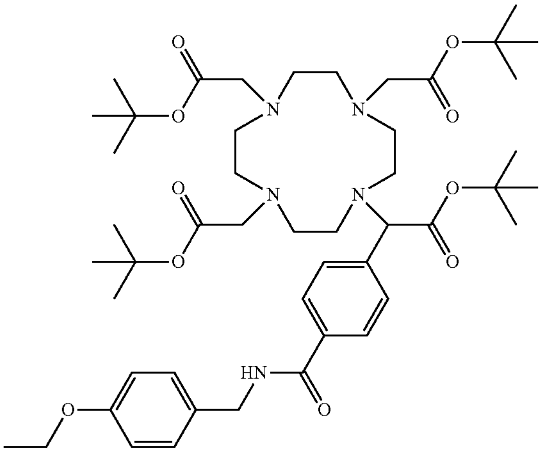

A-4

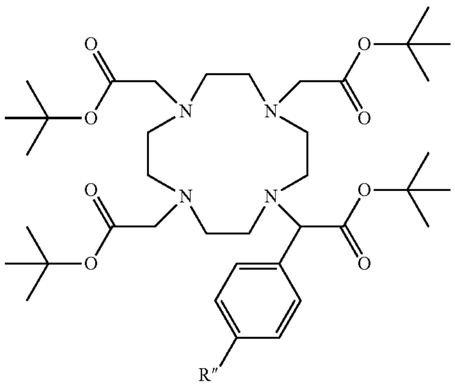

In the present disclosure, unless otherwise specified, all raw materials used are conventional commercially-available products in the art.

In the present disclosure, in a nitrogen atmosphere, a compound with a structure shown in formula A-1, DO3A, potassium carbonate, and acetonitrile are mixed to allow a nucleophilic substitution reaction to obtain a compound with a structure shown in formula A-2.

In the present disclosure, the compound with a structure shown in formula A-1, the DO3A, and the potassium carbonate are in an amount ratio of preferably 1:1:(1.5-2.5) and more preferably 1:1:(1.8-2.2). In the present disclosure, the amount ratio of the compound with a structure shown in formula A-1, the DO3A, and the potassium carbonate is controlled within the above range, which is conducive to the reduction of by-products.

The present disclosure has no particular limitation on a manner of the mixing, and a conventional technical solution in the art can be adopted.

In the present disclosure, the nucleophilic substitution reaction is conducted at preferably 60° C. to 80° C. and more preferably 65° C. to 75° C.; and the nucleophilic substitution reaction is conducted for preferably 12 h to 18 h and more preferably 14 h to 17 h. In the present disclosure, the temperature and time of the nucleophilic substitution reaction are controlled within the above-mentioned ranges, which is conducive to improving a yield of the compound with a structure shown in formula A-2.

In the present disclosure, after the nucleophilic substitution reaction is completed, a product of the nucleophilic substitution reaction is subjected to concentration and column chromatography successively to obtain a compound with a structure shown in formula A-2.

The present disclosure has no particular limitation on a manner of the concentration, as long as the solvent can be removed. In the present disclosure, an eluent used for the column chromatography is preferably a mixed solution of ethyl acetate and methanol in a volume ratio of 5:1.

In the present disclosure, after the compound with a structure shown in formula A-2 is obtained, the compound with a structure shown in formula A-2, THF, methanol, and a lithium hydroxide aqueous solution are mixed to allow a hydrolysis reaction to obtain a first reaction precursor.

In the present disclosure, the compound with a structure shown in formula A-2 and lithium hydroxide in the lithium hydroxide aqueous solution are in an amount ratio of preferably (1-1.5):(3.5-4.5) and more preferably (1.1-1.4):(3.8-4.2). In the present disclosure, the amount ratio of the compound with a structure shown in formula A-2 and the lithium hydroxide in the lithium hydroxide aqueous solution is controlled within the above range, which is conducive to improving the reaction efficiency.

In the present disclosure, the mixing is preferably conducted as follows: the compound with a structure shown in formula A-2 is mixed with a mixture of THF and methanol in a volume ratio of 1:1 to obtain a mixed solution; and then the mixed solution is mixed with the lithium hydroxide aqueous solution.

In the present disclosure, the hydrolysis reaction is conducted preferably at room temperature; and the hydrolysis reaction is conducted for preferably 10 h to 15 h and more preferably 11 h to 13 h. In the present disclosure, the temperature and time of the hydrolysis reaction are controlled within the above-mentioned ranges, which is conducive to improving the yield and purity of a product of the hydrolysis reaction.

In the present disclosure, after the hydrolysis reaction is completed, a product of the hydrolysis reaction is preferably subjected to concentration, dilution with water, pH adjustment, and solvent removal successively to obtain a first reaction precursor.

The present disclosure has no particular limitation on a manner of the concentration, as long as the solvent can be removed. The present disclosure has no particular limitation on a manner of the dilution with water, as long as a concentrated product can be dissolved. In the present disclosure, the pH adjustment is preferably conducted as follows: adjusting a pH with 1 N hydrochloric acid to 7. The present disclosure has no particular limitation on a manner of the solvent removal, as long as the solvent can be removed.

In the present disclosure, after the first reaction precursor is obtained, in a nitrogen atmosphere, the first reaction precursor is mixed with HATU, DCM, an amine, and DIPEA to allow a condensation reaction to obtain a compound with a structure shown in formula A-3.

In the present disclosure, the amine is preferably p-ethoxybenzylamine or 3,3-diphenylpropylamine. In the present disclosure, the compound with a structure shown in formula A-2, the HATU, the amine, and the DIPEA are in an amount ratio of preferably (1-1.5):(2-3):(2-3):(2-3) and more preferably (1.1-1.4):(2.2-2.8):(2.2-2.8):(2.2-2.8). In the present disclosure, the amount ratio of the compound with a structure shown in formula A-2, the HATU, the amine, and the DIPEA is controlled within the above range, which is conducive to increasing a yield of the compound with a structure shown in formula A-3.

In the present disclosure, the mixing is preferably conducted as follows: the first reaction precursor is mixed with the HATU and DCM to obtain a mixed solution; and then the mixed solution is mixed with the amine and DIPEA.

In the present disclosure, the condensation reaction is conducted preferably at room temperature; and the condensation reaction is conducted for preferably 3 h to 6 h and more preferably 3.5 h to 5 h. In the present disclosure, the temperature and time of the condensation reaction are controlled within the above-mentioned ranges, which is conducive to reducing side reactions.

In the present disclosure, after the condensation reaction is completed, a product of the condensation reaction is preferably subjected to DCM addition, water-washing, drying, concentration, and column chromatography successively to obtain a compound with a structure shown in formula A-3.

The present disclosure has no particular limitation on a manner of the DCM addition, as long as the product can be fully dissolved. The present disclosure has no particular limitation on a manner of the water-washing, as long as water-soluble impurities can be removed. The present disclosure has no particular limitation on a manner of the drying, as long as water can be removed. The present disclosure has no particular limitation on a manner of the concentration, as long as the organic solvent can be removed. The present disclosure has no particular limitation on a manner of the column chromatography, as long as the separation and purification can be achieved to obtain the compound with a structure shown in formula A-3.

In the present disclosure, after the compound with a structure shown in formula A-3 is obtained, the compound with a structure shown in formula A-3 and TFA are mixed to allow a t-butyl ester group removal reaction to obtain a compound with a structure shown in formula A-4.

In the present disclosure, a ratio of a mass of the compound with a structure shown in formula A-3 to a volume of the TFA is preferably (0.9-1.5):(3.3-5) and more preferably (1-1.3):(3.5-4.5). In the present disclosure, the ratio of the mass of the compound with a structure shown in formula A-3 to the volume of the TFA is controlled within the above range, which is conducive to increasing a yield of the compound with a structure shown in formula A-4.

The present disclosure has no particular limitation on a manner of the mixing, as long as the components can be thoroughly mixed..

In the present disclosure, the t-butyl ester group removal reaction is conducted at room temperature; and the t-butyl ester group removal reaction is conducted for preferably 10 h to 15 h and more preferably 11 h to 13 h. In the present disclosure, the temperature and time of the t-butyl ester group removal reaction are controlled within the above-mentioned ranges, which is conducive to improving a yield of the compound with a structure shown in formula A-4.

In the present disclosure, after the t-butyl ester group removal reaction is completed, a product of the t-butyl ester group removal reaction is preferably separated through evaporation for TFA removal to obtain a compound with a structure shown in formula A-4.

The present disclosure has no particular limitation on a manner of the evaporation for TFA removal, as long as the TFA can be removed. In the present disclosure, a device for the separation is preferably a reversed-phase liquid chromatography (RPLC) instrument. The present disclosure has no particular limitation on a manner of the separation, as long as the compound with a structure shown in formula A-4 can be separated and purified.

In the present disclosure, after the compound with a structure shown in formula A-4 is obtained, the compound with a structure shown in formula A-4, a gadolinium source, water, and an $M^+$-containing solution are mixed to allow a complexation reaction to obtain the cyclic Gd (III) complex.

In the present disclosure, the compound with a structure shown in formula A-4 and the gadolinium source are preferably in an amount ratio of 1:1. In the present disclosure, the amount ratio of the compound with a structure shown in formula A-4 and the gadolinium source is controlled within the above range, which is beneficial to improving a yield of the cyclic Gd (III) complex.

In the present disclosure, the $M^+$-containing solution is a solution of a metal hydroxide or a glucosamine. In the present disclosure, the metal hydroxide is preferably selected from the group consisting of NaOH, KOH, and LiOH. In the present disclosure, the $M^+$-containing solution has a concentration preferably of 1 N. In the present disclosure, the mixing is preferably conducted as follows: the compound with a structure shown in formula A-4, a gadolinium source, and water are mixed to obtain a mixed solution; and then a pH of the mixed solution is adjusted with an $M^+$-containing solution to 7.

In the present disclosure, the complexation reaction is conducted at preferably 90° C. to 110° C. and more preferably 95° C. to 105° C.; and the complexation reaction is conducted for preferably 5 h to 7 h and more preferably 5.5 h to 6.5 h. In the present disclosure, the temperature and time of the complexation reaction are controlled within the above-mentioned ranges, which is conducive to improving a yield of the cyclic Gd (III) complex.

In the present disclosure, after the complexation reaction is completed, a product of the complexation reaction is preferably separated to obtain the cyclic Gd (III) complex.

In the present disclosure, a device for the separation is preferably an RPLC instrument. The present disclosure has no particular limitation on a manner of the separation, as long as the separation and purification can be achieved.

In the present disclosure, when R is H, R' is H, and R" is selected from the group consisting of H, —COOH, —$CF_3$, —$C(CH_3)_3$, -Ph, —$NO_2$, and —OBn in formula I, the preparation method of the cyclic Gd (III) complex includes the following steps:

S1 in a nitrogen atmosphere, mixing a compound with a structure shown in formula B-1, acetonitrile, DO3A, and potassium carbonate to allow a nucleophilic substitution reaction to obtain a second reaction precursor;

S2. mixing the second reaction precursor obtained in S1 with hydrochloric acid to allow a t-butyl ester group removal reaction to obtain a compound with a structure shown in formula B-2; and S3. mixing the compound with a structure shown in formula B-2 obtained in S2, a gadolinium source, water, and an $M^+$-containing solution to allow a complexation reaction to obtain the cyclic Gd (III) complex, where the $M^+$-containing solution in S3 is a solution of a metal hydroxide or a glucosamine.

B-1

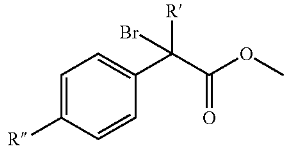

B-2

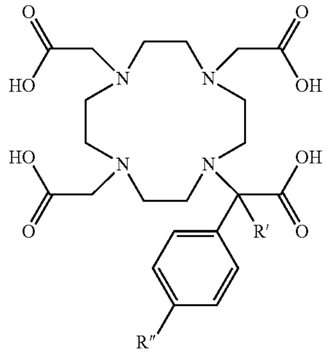

In the present disclosure, in a nitrogen atmosphere, a compound with a structure shown in formula B-1, acetonitrile, DO3A, and potassium carbonate are mixed to allow a nucleophilic substitution reaction to obtain a second reaction precursor.

In the present disclosure, the compound with a structure shown in formula B-1, the DO3A, and the potassium carbonate are in an amount ratio of preferably 1:1:(1.5-2.5) and more preferably 1:1:(1.8-2.2). In the present disclosure, the amount ratio of the compound with a structure shown in formula B-1, the DO3A, and the potassium carbonate is controlled within the above range, which is conducive to improving a yield of a product of the nucleophilic substitution reaction.

The present disclosure has no particular limitation on a manner of the mixing, and a conventional technical solution in the art can be adopted.

In the present disclosure, the nucleophilic substitution reaction is conducted at preferably 60° C. to 80° C. and more preferably 65° C. to 75° C.; and the nucleophilic substitution reaction is conducted for preferably 15 h to 19 h and more preferably 16 h to. 18 h. In the present disclosure, the temperature and time of the nucleophilic substitution reaction are controlled within the above-mentioned ranges, which is conducive to improving a yield of a product of the nucleophilic substitution reaction.

In the present disclosure, after the nucleophilic substitution reaction is completed, a product of the nucleophilic substitution reaction is subjected to filtration and concentration successively.

The present disclosure has no particular limitation on a manner of the filtration, as long as the solid-liquid separation (SLS) can be achieved. The present disclosure has no particular limitation on a manner of the concentration, as long as the solvent can be removed.

In the present disclosure, after the second reaction precursor is obtained, the second reaction precursor is mixed with hydrochloric acid to allow a t-butyl ester group removal reaction to obtain a compound with a structure shown in formula B-2.

The present disclosure has no particular limitation on a manner of the mixing, as long as the components can be thoroughly mixed. In the present disclosure, the hydrochloric acid preferably has a concentration of 6 N. In the present disclosure, a ratio of a molar mass of the compound with a structure shown in formula B-1 to a volume of the hydrochloric acid is preferably 1 mmol: (5-7) mL.

In the present disclosure, the t-butyl ester group removal reaction is conducted at preferably 100° C. to 120° C. and more preferably 105° C. to 110° C.; and the t-butyl ester group removal reaction is conducted for preferably 15 h to 19 h and more preferably 16 h to 18 h. In the present disclosure, the temperature and time of the t-butyl ester group removal reaction are controlled within the above-mentioned ranges, which is conducive to improving a yield of the compound with a structure shown in formula B-2.

In the present disclosure, after the t-butyl ester group removal reaction is completed, a product of the t-butyl ester group removal reaction is preferably separated to obtain a compound with a structure shown in formula B-2.

In the present disclosure, a device for the separation is preferably an RPLC instrument. The present disclosure has no particular limitation on a manner of the separation, as long as the separation and purification can be achieved.

In the present disclosure, after the compound with a structure shown in formula B-2 is obtained, the compound with a structure shown in formula B-2, a gadolinium source, water, and an $M^+$-containing solution are mixed to allow a complexation reaction to obtain the cyclic Gd (III) complex.

In the present disclosure, the compound with a structure shown in formula B-2 and the gadolinium source are preferably in an amount ratio of 1:1. In the present disclosure, the $M^+$-containing solution is a solution of a metal hydroxide or a glucosamine. In the present disclosure, the metal hydroxide is preferably selected from the group consisting of NaOH, KOH, and LiOH. In the present disclosure, the $M^+$-containing solution has a concentration preferably of 1 N. In the present disclosure, the mixing is preferably conducted as follows: the compound with a structure shown in formula B-2, a gadolinium source, and water are mixed to obtain a mixed solution; and then a pH of the mixed solution is adjusted with an $M^+$-containing solution to 7.

In the present disclosure, the complexation reaction is conducted at preferably 90° C. to 110° C. and more preferably 95° C. to 105° C.; and the complexation reaction is conducted for preferably 5 h to 7 h and more preferably 5.5 h to 6.5 h. In the present disclosure, the temperature and time of the complexation reaction are controlled within the above-mentioned ranges, which is conducive to improving a yield of the cyclic Gd (III) complex.

In the present disclosure, after the complexation reaction is completed, a product of the complexation reaction is preferably separated to obtain the cyclic Gd (III) complex.

In the present disclosure, a device for the separation is preferably an RPLC instrument. The present disclosure has no particular limitation on a manner of the separation, as long as the separation and purification can be achieved.

In the present disclosure, when R is selected from the group consisting of $C_1$-$C_4$ alkyl, $-CH_2OH$, $-CH(CH_3)OH$, $-CH_2CH_2OH$, $-CH_2Ph$, $-(CH_2)_2Ph$, $-(CH_2)_3Ph$, $-(CH_2)_3NH_2$, and $-(CH_2)_4Ph$, R' is H, and R" is $-COOH$ in formula I, the preparation method of the cyclic Gd (III) complex includes the following steps:

(a) mixing a compound with a structure shown in formula C-1, a compound with a structure shown in chiral cyclen, and acetonitrile to allow a first nucleophilic substitution reaction to obtain a compound with a structure shown in formula C-2;

(b) in a nitrogen atmosphere, mixing the compound with a structure shown in formula C-2 obtained in step (a), acetonitrile, potassium carbonate, and ethyl bromoacetate to allow a second nucleophilic substitution reaction to obtain a compound with a structure shown in formula C-3;

(c) mixing the compound with a structure shown in formula C-3 obtained in step (b), THF, methanol, and a lithium hydroxide aqueous solution to allow a hydrolysis reaction to obtain a compound with a structure shown in formula C-4; and (d) mixing the compound with a structure shown in formula C-4 obtained in step (c), a gadolinium source, water, and an $M^+$-containing solution to allow a complexation reaction to obtain the cyclic Gd (III) complex, where the $M^+$-containing solution in step (d) is a solution of a metal hydroxide or a glucosamine.

C-1

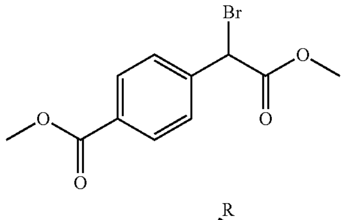

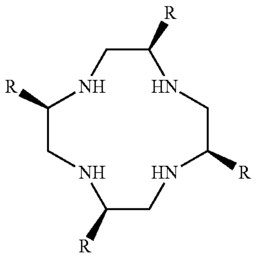

Chiral cyclen

-continued

C-2

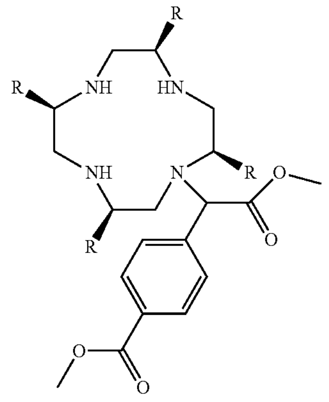

C-3

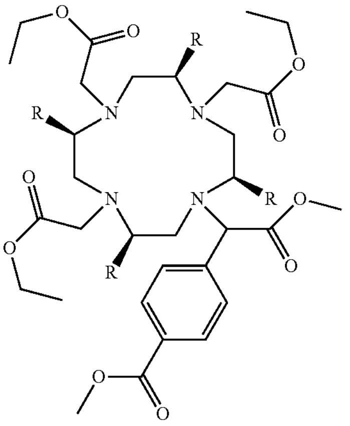

C-4

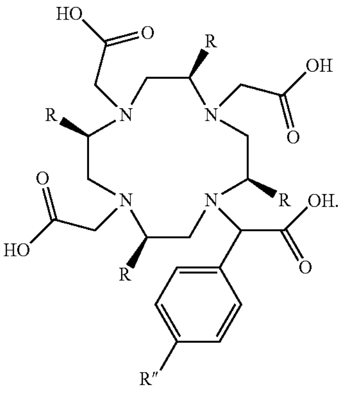

In the present disclosure, a compound with a structure shown in formula C-1, a compound with a structure shown in chiral cyclen, and acetonitrile are mixed to allow a first nucleophilic substitution reaction to obtain a compound with a structure shown in formula C-2.

The present disclosure has no particular limitation on a manner of the mixing, as long as the components can be thoroughly mixed.

In the present disclosure, the compound with a structure shown in formula C-1 and the compound with a structure shown in chiral cyclen are preferably in an amount ratio of 1:1.

In the present disclosure, the first nucleophilic substitution reaction is conducted preferably at room temperature; and the first nucleophilic substitution reaction is conducted for preferably 16 h to 20 h and more preferably 17 h to 19 h. In the present disclosure, the temperature and time of the first nucleophilic substitution reaction are controlled within the above-mentioned ranges, which is conducive to improving a yield of the compound with a structure shown in formula C-2.

In the present disclosure, after the first nucleophilic substitution reaction is completed, a product of the first nucleophilic substitution reaction is subjected to a first solvent removal, dissolution, a first extraction, pH adjustment, a second extraction, and a second solvent removal successively to obtain a compound with a structure shown in formula C-2.

The present disclosure has no particular limitation on a manner of the first solvent removal, as long as the organic solvent can be removed. In the present disclosure, a reagent used for the dissolution is preferably ethyl acetate. In the present disclosure, a reagent used for the first extraction is preferably 1 N hydrochloric acid; and the first extraction is preferably conducted 3 times. In the present disclosure, the pH adjustment is preferably conducted as follows: adjusting a pH with a potassium carbonate solution to 10. In the present disclosure, a reagent used for the second extraction is preferably DCM; and the second extraction is preferably conducted 3 times. The present disclosure has no particular limitation on a manner of the second solvent removal, as long as the organic solvent can be removed.

In the present disclosure, after the compound with a structure shown in formula C-2 is obtained, in a nitrogen atmosphere, the compound with a structure shown in formula C-2, acetonitrile, potassium carbonate, and ethyl bromoacetate are mixed to allow a second nucleophilic substitution reaction to obtain a compound with a structure shown in formula C-3.

In the present disclosure, the mixing is preferably conducted as follows: the compound with a structure shown in formula C-2 and acetonitrile are mixed to obtain a mixed solution; and then the potassium carbonate and tert-butyl bromoacetate are successively added to the mixed solution.

In the present disclosure, the compound with a structure shown in formula C-2, the potassium carbonate, and the tert-butyl bromoacetate are in an amount ratio of preferably 1:4.9:5.3 and more preferably 1:5:5.2. In the present disclosure, the amount ratio of the compound with a structure shown in formula C-2, the potassium carbonate, and the tert-butyl bromoacetate is controlled within the above range, which is conducive to increasing a yield of the compound with a structure shown in formula C-3.

In the present disclosure, the second nucleophilic substitution reaction is conducted at room temperature; and the second nucleophilic substitution reaction is conducted for preferably 16 h to 20 h and more preferably 17 h to 19 h. In the present disclosure, the temperature and time of the second nucleophilic substitution reaction are controlled within the above-mentioned ranges, which is conducive to improving a yield of the compound with a structure shown in formula C-3.

In the present disclosure, after the second nucleophilic substitution reaction is completed, a product of the second nucleophilic substitution reaction is preferably subjected to filtration, concentration, and column chromatography to obtain a compound with a structure shown in formula C-3.

The present disclosure has no particular limitation on a manner of the filtration, as long as the SLS can be achieved. The present disclosure has no particular limitation on a manner of the concentration, as long as the solvent can be removed. In the present disclosure, an eluent used for the column chromatography is preferably a mixed solution of ethyl acetate and methanol in a volume ratio of 10:1.

In the present disclosure, after the compound with a structure shown in formula C-3 is obtained, the compound with a structure shown in formula C-3, THF, methanol, and a lithium hydroxide aqueous solution are mixed to allow a hydrolysis reaction to obtain a compound with a structure shown in formula C-4.

In the present disclosure, the compound with a structure shown in formula C-3 and lithium hydroxide in the lithium hydroxide aqueous solution are in an amount ratio of preferably (1-1.5):(3.5-4.5) and more preferably (1.1-1.4):(3.8-4.2). In the present disclosure, the amount ratio of the compound with a structure shown in formula C-3 and the lithium hydroxide in the lithium hydroxide aqueous solution is controlled within the above range, which is conducive to improving a yield of the compound with a structure shown in formula C-4.

In the present disclosure, the mixing is preferably conducted as follows: the compound with a structure shown in formula C-3 is mixed with a mixture of THF and methanol in a volume ratio of 1:1 to obtain a mixed solution; and then the mixed solution is mixed with the lithium hydroxide aqueous solution.

In the present disclosure, the hydrolysis reaction is conducted preferably at room temperature; and the hydrolysis reaction is conducted for preferably 4 h to 8 h and more preferably 5 h to 7 h. In the present disclosure, the temperature and time of the hydrolysis reaction are controlled within the above-mentioned ranges, which is conducive to improving a yield of the compound with a structure shown in formula C-4.

In the present disclosure, after the hydrolysis reaction is completed, a product of the hydrolysis reaction is preferably subjected to concentration, dilution with water, pH adjustment, and separation successively to obtain a compound with a structure shown in formula C-4.

The present disclosure has no particular limitation on a manner of the concentration, as long as the solvent can be removed. The present disclosure has no particular limitation on a manner of the dilution with water, as long as a concentrated product can be dissolved. In the present disclosure, the pH adjustment is preferably conducted as follows: adjusting a pH with 1 N hydrochloric acid to 7. In the present disclosure, a device for the separation is preferably an RPLC instrument. The present disclosure has no particular limitation on a manner of the separation, as long as the compound with a structure shown in formula C-4 can be separated and purified.

In the present disclosure, after the compound with a structure shown in formula C-4 is obtained, the compound with a structure shown in formula C-4, a gadolinium source, water, and an $M^+$-containing solution are mixed to allow a complexation reaction to obtain the cyclic Gd (III) complex.

In the present disclosure, the compound with a structure shown in formula C-4 and the gadolinium source are preferably in an amount ratio of 1:1. In the present disclosure, the $M^+$-containing solution is a solution of a metal hydroxide or a glucosamine. In the present disclosure, the metal hydroxide is preferably selected from the group consisting of NaOH, KOH, and LiOH. In the present disclosure, the $M^+$-containing solution has a concentration preferably of 1 N. In the present disclosure, the mixing is preferably conducted as follows: the compound with a structure shown in formula C-4, a gadolinium source, and water are mixed to obtain a mixed solution; and then a pH of the mixed solution is adjusted with an $M^+$-containing solution to 7.

In the present disclosure, the complexation reaction is conducted at preferably 90° C. to 110° C. and more preferably 95° C. to 105° C.; and the complexation reaction is conducted for preferably 5 h to 7 h and more preferably 5.5 h to 6.5 h. In the present disclosure, the temperature and time of the complexation reaction are controlled within the above-mentioned ranges, which is conducive to improving a yield of the cyclic Gd (III) complex.

In the present disclosure, after the complexation reaction is completed, a product of the complexation reaction is preferably separated to obtain the cyclic Gd (III) complex.

In the present disclosure, a device for the separation is preferably an RPLC instrument. The present disclosure has no particular limitation on a manner of the separation, as long as the separation and purification can be achieved.

In the present disclosure, when R is selected from the group consisting of $C_1$-$C_4$ alkyl, $-CH_2OH$, $-CH(CH_3)OH$, $-CH_2CH_2OH$, $-CH_2Ph$, $-(CH_2)_2Ph$, $-(CH_2)_3Ph$, $-(CH_2)_3NH_2$, and $-(CH_2)_4Ph$, R' is

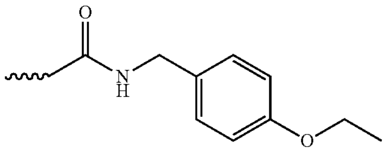

or

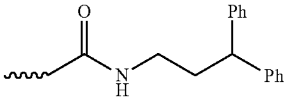

in formula I, the preparation method of the cyclic Gd (III) complex includes the following steps:

1) mixing a compound with a structure shown in formula A-1, a compound with a structure shown in chiral cyclen, and acetonitrile to allow a first nucleophilic substitution reaction to obtain a compound with a structure shown in formula D-2;
2) in a nitrogen atmosphere, mixing the compound with a structure shown in formula D-2 obtained in step 1), acetonitrile, potassium carbonate, and tert-butyl bromoacetate to allow a second nucleophilic substitution reaction to obtain a compound with a structure shown in formula D-3;
3) mixing the compound with a structure shown in formula D-3 obtained in step 2), THF, methanol, and a lithium hydroxide aqueous solution to allow an ester hydrolysis reaction to obtain a third reaction precursor;
4) in a nitrogen atmosphere, mixing the third reaction precursor obtained in step 3) with HATU, DCM, an amine compound, and DIPEA to allow a condensation reaction to obtain a compound with a structure shown in formula D-4;
5) in a nitrogen atmosphere, mixing the compound with a structure shown in formula D-4 obtained in step 4) and TFA to allow a t-butyl ester group removal reaction to obtain a compound with a structure shown in formula D-5; and
6) mixing the compound with a structure shown in formula D-5 obtained in step 5), a gadolinium source, water, and an $M^+$-containing solution to allow a complexation reaction to obtain the cyclic Gd (III) complex, where the $M^+$-containing solution in step 6) is a solution of a metal hydroxide or a glucosamine.

A-1

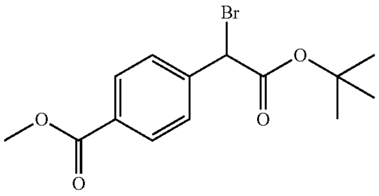

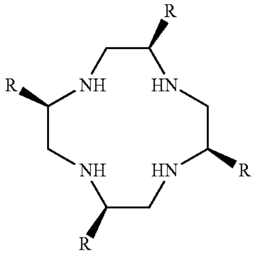

Chiral cyclen

D-2

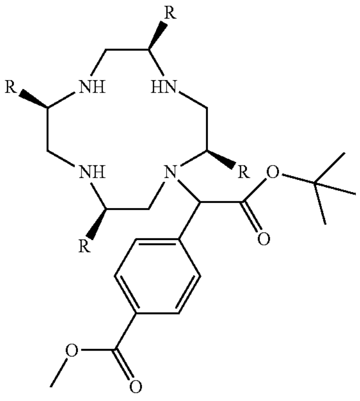

D-3

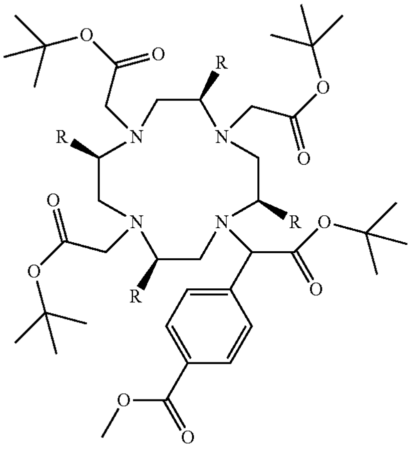

-continued

D-4

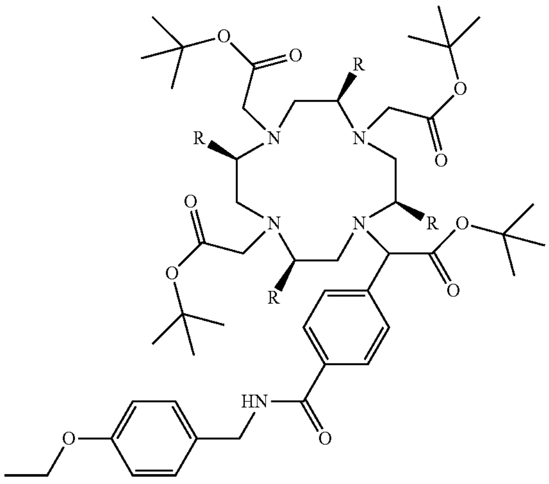

D-5

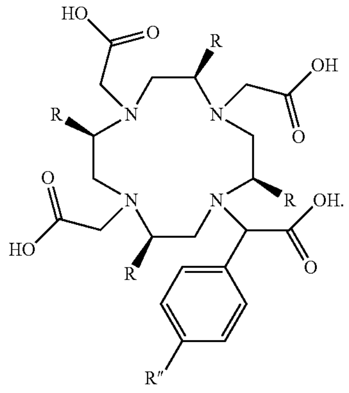

In the present disclosure, a compound with a structure shown in formula A-1, a compound with a structure shown in chiral cyclen, and acetonitrile are mixed to allow a first nucleophilic substitution reaction to obtain a compound with a structure shown in formula D-2.

The present disclosure has no particular limitation on a manner of the mixing, as long as the components can be thoroughly mixed.

In the present disclosure, the compound with a structure shown in formula A-1 and the compound with a structure shown in chiral cyclen are preferably in an amount ratio of 1:1.

In the present disclosure, the first nucleophilic substitution reaction is conducted at preferably 70° C. to 90° C. and more preferably 75° C. to 85° C.; and the first nucleophilic substitution reaction is conducted for preferably 6 h to 8 h and more preferably 6.5 h to 7.5 h. In the present disclosure, the temperature and time of the first nucleophilic substitution reaction are controlled within the above-mentioned ranges, which is conducive to improving a yield of the compound with a structure shown in formula D-2.

In the present disclosure, after the first nucleophilic substitution reaction is completed, a product of the first nucleophilic substitution reaction is preferably subjected to concentration and column chromatography successively.

The present disclosure has no particular limitation on a manner of the concentration, as long as the solvent can be removed. In the present disclosure, an eluent used for the column chromatography is preferably a mixed solution of ethyl acetate and methanol in a volume ratio of 5:1.

In the present disclosure, after the compound with a structure shown in formula D-2 is obtained, in a nitrogen atmosphere, the compound with a structure shown in formula D-2, acetonitrile, potassium carbonate, and tert-butyl bromoacetate are mixed to allow a second nucleophilic substitution reaction to obtain a compound with a structure shown in formula D-3.

In the present disclosure, the compound with a structure shown in formula D-2, the potassium carbonate, and the tert-butyl bromoacetate are in an amount ratio of preferably 1:4.9:5.3 and more preferably 1:5:5.2. In the present disclosure, the amount ratio of the compound with a structure shown in formula D-2, the potassium carbonate, and the tert-butyl bromoacetate is controlled within the above range, which is conducive to increasing a yield of the compound with a structure shown in formula D-3.

In the present disclosure, the second nucleophilic substitution reaction is conducted preferably at room temperature; and the second nucleophilic substitution reaction is conducted for preferably 16 h to 20 h and more preferably 17 h to 19 h. In the present disclosure, the temperature and time of the second nucleophilic substitution reaction are controlled within the above-mentioned ranges, which is conducive to improving a yield of the compound with a structure shown in formula D-3.

In the present disclosure, after the second nucleophilic substitution reaction is completed, a product of the second nucleophilic substitution reaction is preferably subjected to filtration, concentration, and column chromatography to obtain a compound with a structure shown in formula D-3.

The present disclosure has no particular limitation on a manner of the filtration, as long as the SLS can be achieved. The present disclosure has no particular limitation on a manner of the concentration, as long as the solvent can be removed. In the present disclosure, an eluent used for the column chromatography is preferably a mixed solution of ethyl acetate and methanol in a volume ratio of 20:1.

In the present disclosure, after the compound with a structure shown in formula D-3 is obtained, the compound with a structure shown in formula D-3, THF, methanol, and a lithium hydroxide aqueous solution are mixed to allow an ester hydrolysis reaction to obtain a third reaction precursor.

In the present disclosure, the compound with a structure shown in formula D-3 and lithium hydroxide in the lithium hydroxide aqueous solution are in an amount ratio of preferably (1.5-2):(4.9-5.5) and more preferably (1.6-1.8):(5-5.2). In the present disclosure, the amount ratio of the compound with a structure shown in formula D-3 and the lithium hydroxide in the lithium hydroxide aqueous solution is controlled within the above range, which is conducive to improving a yield of a product of the ester hydrolysis reaction.

In the present disclosure, the mixing is preferably conducted as follows: the compound with a structure shown in formula D-3 is mixed with a mixture of THF and methanol in a volume ratio of 1:1 to obtain a mixed solution; and then the mixed solution is mixed with the lithium hydroxide aqueous solution.

In the present disclosure, the ester hydrolysis reaction is conducted at room temperature; and the ester hydrolysis reaction is conducted for preferably 4 h to 8 h and more preferably 5 h to 7 h. In the present disclosure, the temperature and time of the ester hydrolysis reaction are controlled within the above-mentioned ranges, which is conducive to improving a yield of a product of the ester hydrolysis reaction.

In the present disclosure, after the ester hydrolysis reaction is completed, a product of the ester hydrolysis reaction is preferably subjected to concentration, dilution with water, pH adjustment, and solvent removal successively to obtain a third reaction precursor.

The present disclosure has no particular limitation on a manner of the concentration, as long as the solvent can be removed. The present disclosure has no particular limitation on a manner of the dilution with water, as long as a concentrated product can be dissolved. In the present disclosure, the pH adjustment is preferably conducted as follows: adjusting a pH with 1 N hydrochloric acid to 7. The present disclosure has no particular limitation on a manner of the solvent removal, as long as the solvent can be removed.

In the present disclosure, after the third reaction precursor is obtained, in a nitrogen atmosphere, the third reaction precursor is mixed with HATU, DCM, an amine compound, and DIPEA to allow a condensation reaction to obtain a compound with a structure shown in formula D-4.

In the present disclosure, the amine compound is preferably p-ethoxybenzylamine or 3,3-diphenylpropylamine. In the present disclosure, the compound with a structure shown in formula D-3, the HATU, the amine compound, and the DIPEA are in an amount ratio of preferably (1.5-2):(3.2-3.6):(3.2-3.6):(3.2-3.6) and more preferably (1.6-1.8):(3.3-3.5):(3.3-3.5):(3.3-3.5). In the present disclosure, the amount ratio of the compound with a structure shown in formula D-3, the HATU, the amine compound, and the DIPEA is controlled within the above range, which is conducive to increasing a yield of the compound with a structure shown in formula D-4.

In the present disclosure, the mixing is preferably conducted as follows: the third reaction precursor is mixed with the DCM to obtain a mixed solution; and then the mixed solution is mixed with the HATU, amine compound, and DIPEA.

In the present disclosure, the condensation reaction is conducted preferably at room temperature; and the condensation reaction is conducted for preferably 3 h to 6 h and more preferably 3.5 h to 5 h. In the present disclosure, the temperature and time of the condensation reaction are controlled within the above-mentioned ranges, which is conducive to improving a yield of the compound with a structure shown in formula D-4.

In the present disclosure, after the condensation reaction is completed, a product of the condensation reaction is preferably subjected to solvent removal and column chromatography successively to obtain a compound with a structure shown in formula D-4.

The present disclosure has no particular limitation on a manner of the solvent removal, as long as the organic solvent can be removed. In the present disclosure, an eluent used for the column chromatography is preferably a mixed solution of ethyl acetate and methanol in a volume ratio of 10:1.

In the present disclosure, after the compound with a structure shown in formula D-4 is obtained, in a nitrogen atmosphere, the compound with a structure shown in formula D-4 and TFA are mixed to allow a t-butyl ester group removal reaction to obtain a compound with a structure shown in formula D-5.

In the present disclosure, a ratio of a mass of the compound with a structure shown in formula D-4 to a volume of the TFA is preferably (0.8-1.2):(3.3-5) and more preferably (0.9-1.1):(3.5-4.5). In the present disclosure, the ratio of the mass of the compound with a structure shown in formula D-4 to the volume of the TFA is controlled within the above range, which is conducive to increasing a yield of the compound with a structure shown in formula D-5.

The present disclosure has no particular limitation on a manner of the mixing, as long as the components can be thoroughly mixed.

In the present disclosure, the t-butyl ester group removal reaction is conducted preferably at room temperature; and the t-butyl ester group removal reaction is conducted for preferably 10 h to 15 h and more preferably 11 h to 13 h. In the present disclosure, the temperature and time of the t-butyl ester group removal reaction are controlled within the above-mentioned ranges, which is conducive to improving a yield of the compound with a structure shown in formula D-5.

In the present disclosure, after the t-butyl ester group removal reaction is completed, a product of the t-butyl ester group removal reaction is subjected to concentration and separation successively to obtain a compound with a structure shown in formula D-5.

The present disclosure has no particular limitation on a manner of the concentration, as long as the solvent can be removed. In the present disclosure, a device for the separation is preferably an RPLC instrument. The present disclosure has no particular limitation on a manner of the separation, as long as the separation and purification can be achieved.

In the present disclosure, after the compound with a structure shown in formula D-5 is obtained, the compound with a structure shown in formula D-5, a gadolinium source, water, and an $M^+$-containing solution are mixed to allow a complexation reaction to obtain the cyclic Gd (III) complex.

In the present disclosure, the compound with a structure shown in formula D-5 and the gadolinium source are preferably in an amount ratio of 1:1. In the present disclosure, the $M^+$-containing solution is a solution of a metal hydroxide or a glucosamine. In the present disclosure, the metal hydroxide is preferably selected from the group consisting of NaOH, KOH, and LiOH. In the present disclosure, the $M^+$-containing solution has a concentration preferably of 1 N. In the present disclosure, the mixing is preferably conducted as follows: the compound with a structure shown in formula D-5, a gadolinium source, and water are mixed to obtain a mixed solution; and then a pH of the mixed solution is adjusted with an $M^+$-containing solution to 7.

In the present disclosure, the complexation reaction is conducted at preferably 90° C. to 110° C. and more preferably 95° C. to 105° C.; and the complexation reaction is conducted for preferably 5 h to 7 h and more preferably 5.5 h to 6.5 h. In the present disclosure, the temperature and time of the complexation reaction are controlled within the above-mentioned ranges, which is conducive to improving a yield of the cyclic Gd (III) complex.

In the present disclosure, after the complexation reaction is completed, a product of the complexation reaction is preferably separated to obtain the cyclic Gd (III) complex.

In the present disclosure, a device for the separation is preferably an RPLC instrument. The present disclosure has no particular limitation on a manner of the separation, as long as the separation and purification can be achieved.

In the present disclosure, when R is selected from the group consisting of $C_1$-$C_4$ alkyl, —$CH_2OH$, —$CH(CH_3)OH$, —$CH_2CH_2OH$, —$CH_2Ph$, —$(CH_2)_2Ph$, —$(CH_2)_3Ph$, —$(CH_2)_3NH_2$, and —$(CH_2)_4Ph$, R' is H, and R" is selected from the group consisting of H, —$CF_3$, —$C(CH_3)_3$, -Ph, —$NO_2$, and —OBn in formula I, the preparation method of the cyclic Gd (III) complex includes the following steps:

(1') in a nitrogen atmosphere, mixing a compound with a structure shown in formula E-1, a compound with a structure shown in chiral cyclen, and acetonitrile to allow a first nucleophilic substitution reaction to obtain a compound with a structure shown in formula E-2;

(2') in a nitrogen atmosphere, mixing the compound with a structure shown in formula E-2 obtained in step (1'), acetonitrile, potassium carbonate, and tert-butyl bromoacetate to allow a second nucleophilic substitution reaction to obtain a compound with a structure shown in formula E-3;

(3') mixing the compound with a structure shown in formula E-3 obtained in step (2'), THF, methanol, and a lithium hydroxide aqueous solution to allow an ester hydrolysis reaction, and subjecting a product of the ester hydrolysis reaction to concentration, dilution, and pH adjustment successively to obtain a compound with a structure shown in formula E-4; and (4') mixing the compound with a structure shown in formula E-4 obtained in step (3'), a gadolinium source, water, and an $M^+$-containing solution to allow a complexation reaction to obtain the cyclic Gd (III) complex, where the $M^+$-containing solution in step (4') is a solution of a metal hydroxide or a glucosamine.

E-1

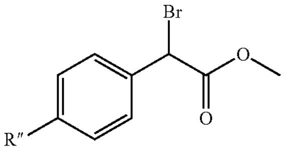

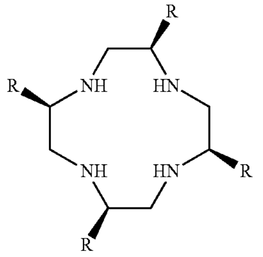

Chiral cyclen

E-2

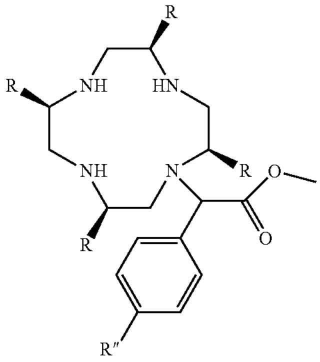

-continued

E-3

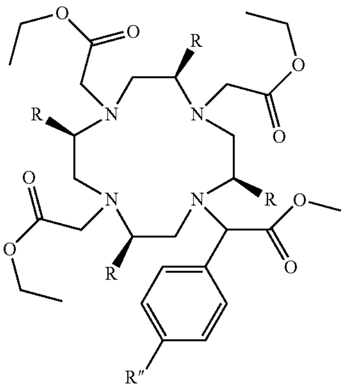

E-4

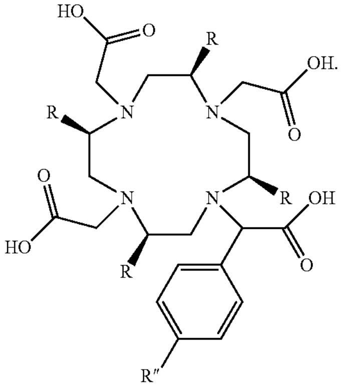

In the present disclosure, in a nitrogen atmosphere, a compound with a structure shown in formula E-1, a compound with a structure shown in chiral cyclen, and acetonitrile are mixed to allow a first nucleophilic substitution reaction to obtain a compound with a structure shown in formula E-2.

The present disclosure has no particular limitation on a manner of the mixing, as long as the components can be thoroughly mixed.

In the present disclosure, the compound with a structure shown in formula E-1 and the compound with a structure shown in chiral cyclen are preferably in an amount ratio of 1:1.

In the present disclosure, the first nucleophilic substitution reaction is conducted preferably at room temperature; and the first nucleophilic substitution reaction is conducted for preferably 15 h to 22 h and more preferably 17 h to 20 h. In the present disclosure, the temperature and time of the first nucleophilic substitution reaction are controlled within the above-mentioned ranges, which is conducive to improving a yield of the compound with a structure shown in formula E-2.

In the present disclosure, after the first nucleophilic substitution reaction is completed, a product of the first nucleophilic substitution reaction is preferably subjected to concentration and column chromatography successively.

The present disclosure has no particular limitation on a manner of the concentration, as long as the solvent can be removed. In the present disclosure, an eluent used for the column chromatography is preferably a mixed solution of ethyl acetate and methanol in a volume ratio of 5:1.

In the present disclosure, after the compound with a structure shown in formula E-2 is obtained, in a nitrogen atmosphere, the compound with a structure shown in formula E-2, acetonitrile, potassium carbonate, and ethyl bromoacetate are mixed to allow a second nucleophilic substitution reaction to obtain a compound with a structure shown in formula E-3.

In the present disclosure, the compound with a structure shown in formula E-2, the potassium carbonate, and the ethyl bromoacetate are in an amount ratio of preferably 1:(4.9-5.3) and more preferably 1:(5-5.2). In the present disclosure, the amount ratio of the compound with a structure shown in formula E-2, the potassium carbonate, and the tert-butyl bromoacetate is controlled within the above range, which is conducive to increasing a yield of the compound with a structure shown in formula E-3.

In the present disclosure, the second nucleophilic substitution reaction is conducted preferably at room temperature; and the second nucleophilic substitution reaction is conducted for preferably 16 h to 20 h and more preferably 17 h to 19 h. In the present disclosure, the temperature and time of the second nucleophilic substitution reaction are controlled within the above-mentioned ranges, which is conducive to improving a yield of the compound with a structure shown in formula E-3.

In the present disclosure, after the second nucleophilic substitution reaction is completed, a product of the second nucleophilic substitution reaction is preferably subjected to filtration, concentration, and column chromatography to obtain a compound with a structure shown in formula E-3.

The present disclosure has no particular limitation on a manner of the filtration, as long as the SLS can be achieved. The present disclosure has no particular limitation on a manner of the concentration, as long as the solvent can be removed. In the present disclosure, an eluent used for the column chromatography is preferably a mixed solution of ethyl acetate and methanol in a volume ratio of 10:1.

In the present disclosure, after the compound with a structure shown in formula E-3 is obtained, the compound with a structure shown in formula E-3, THF, methanol, and a lithium hydroxide aqueous solution are mixed to allow an ester hydrolysis reaction; and then a product of the ester hydrolysis reaction is subjected to concentration, dilution, and pH adjustment successively to obtain a compound with a structure shown in formula E-4.

In the present disclosure, the compound with a structure shown in formula E-3 and lithium hydroxide in the lithium hydroxide aqueous solution are in an amount ratio of preferably (1-1.5):(3.5-4.4) and more preferably (1.1-1.4):(3.6-4.1). In the present disclosure, the amount ratio of the compound with a structure shown in formula E-3 and the lithium hydroxide in the lithium hydroxide aqueous solution is controlled within the above range, which is conducive to improving a yield of the compound with a structure shown in formula E-4.

In the present disclosure, the mixing is preferably conducted as follows: the compound with a structure shown in formula E-3 is mixed with a mixture of THF and methanol in a volume ratio of 1:1 to obtain a mixed solution; and then the mixed solution is mixed with the lithium hydroxide aqueous solution.

In the present disclosure, the ester hydrolysis reaction is conducted preferably at room temperature; and the ester hydrolysis reaction is conducted for preferably 4 h to 8 h and more preferably 5 h to 7 h. In the present disclosure, the temperature and time of the ester hydrolysis reaction are controlled within the above-mentioned ranges, which is conducive to improving a yield of the compound with a structure shown in formula E-4.

The present disclosure has no particular limitation on a manner of the concentration, as long as the solvent can be removed. The present disclosure has no particular limitation on a manner of the dilution with water, as long as a concentrated product can be dissolved. In the present disclosure, the pH adjustment is preferably conducted as follows: adjusting a pH with 1 N hydrochloric acid to 7.

In the present disclosure, after the pH adjustment is completed, a product obtained after the pH adjustment is preferably separated to obtain a compound with a structure shown in formula E-4.

In the present disclosure, a device for the separation is preferably an RPLC instrument. The present disclosure has no particular limitation on a manner of the separation, as long as the separation and purification can be achieved.

In the present disclosure, after the compound with a structure shown in formula E-4 is obtained, the compound with a structure shown in formula E-4, a gadolinium source, water, and an $M^+$-containing solution are mixed to allow a complexation reaction to obtain the cyclic Gd (III) complex.

In the present disclosure, the compound with a structure shown in formula E-4 and the gadolinium source are preferably in an amount ratio of 1:1. In the present disclosure, the $M^+$-containing solution is a solution of a metal hydroxide or a glucosamine. In the present disclosure, the metal hydroxide is preferably selected from the group consisting of NaOH, KOH, and LiOH. In the present disclosure, the $M^+$-containing solution has a concentration preferably of 1 N. In the present disclosure, the mixing is preferably conducted as follows: the compound with a structure shown in formula E-4, a gadolinium source, and water are mixed to obtain a mixed solution; and then a pH of the mixed solution is adjusted with an $M^+$-containing solution to 7.

In the present disclosure, the complexation reaction is conducted at preferably 90° C. to 110° C. and more preferably 95° C. to 105° C.; and the complexation reaction is conducted for preferably 5 h to 7 h and more preferably 5.5 h to 6.5 h. In the present disclosure, the temperature and time of the complexation reaction are controlled within the above-mentioned ranges, which is conducive to improving a yield of the cyclic Gd (III) complex.

In the present disclosure, after the complexation reaction is completed, a product of the complexation reaction is preferably separated to obtain the cyclic Gd (III) complex.

In the present disclosure, a device for the separation is preferably an RPLC instrument. The present disclosure has no particular limitation on a manner of the separation, as long as the separation and purification can be achieved.

In the present disclosure, the RPLC can achieve the effective separation of a Gd (III) complex from a ligand and an inorganic salt to obtain a high-purity Gd (III) complex for MRI.

The present disclosure also provides a pharmaceutical composition including the cyclic Gd (III) complex described in the above technical solution.

The present disclosure also provides use of the cyclic Gd (III) complex or the pharmaceutical composition described in the above technical solution in MRI. In the present disclosure, the cyclic Gd (III) complex or the pharmaceutical composition is preferably used as an MRI contrast agent targeting the liver and gallbladder.

The technical solutions of the present disclosure will be clearly and completely described below in conjunction with the examples of the present disclosure. Apparently, the described examples are merely some rather than all of the examples of the present disclosure. All other examples obtained by a person of ordinary skill in the art based on the examples of the present disclosure without creative efforts shall fall within the protection scope of the present disclosure.

Example 1

A cyclic Gd (III) complex with a chemical structure shown in formula I was provided, where in formula I, R was H, R' was H, and R" was

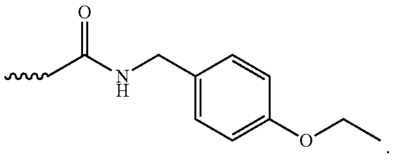

The cyclic Gd (III) complex in this example was denoted as complex GdL1.

A preparation method of the cyclic Gd (III) complex included the following steps

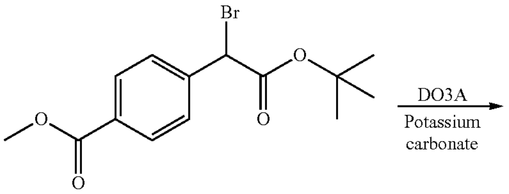

A-1

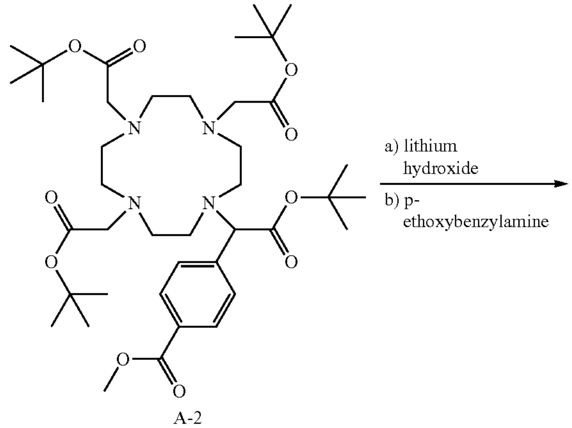

A-2

-continued

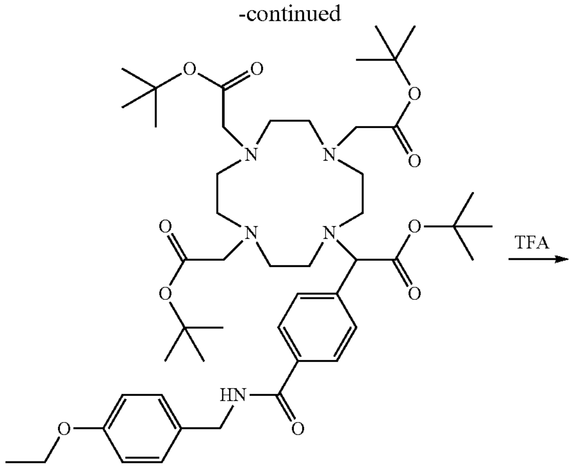

A-3

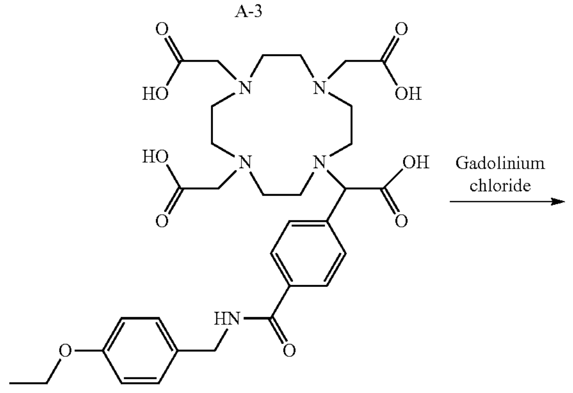

A-4

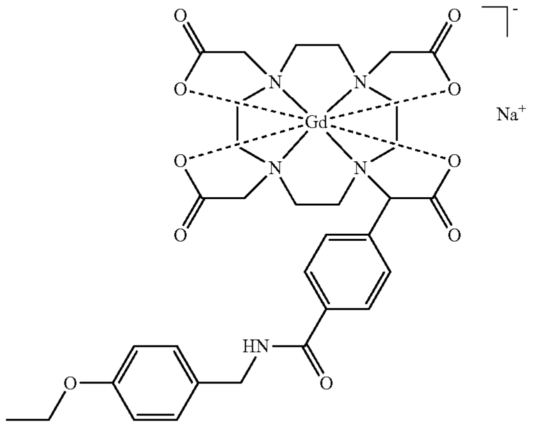

GdL1

R' = H
R'' =

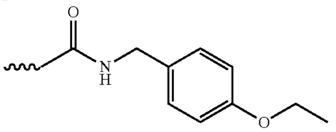

(1) A compound with a structure shown in formula A-1 (1.0 g, 3 mmol), DO3A (1.6 g, 3 mmol), and potassium carbonate (0.6 g, 6 mmol) were dissolved in 20 mL of acetonitrile, a resulting solution was heated to 70° C. and stirred under nitrogen protection to allow a nucleophilic substitution reaction for 16 h, and a product of the nucleophilic substitution reaction was subjected to concentration and purification through silica gel column chromatography (ethyl acetate:methanol=5:1) to obtain a compound with a structure shown in formula A-2 (yield: 76%, $^{1}H$ NMR (400 MHz, $CDCl_3$) δ (ppm): 8.00 (d, 2H, J=8.40 Hz), 7.54 (d, 2H, J=8.40 Hz), 4.52 (s, 1H), 3.92 (s, 3H), 3.33 (s, 2H), 3.18 (s, 3H), 2.80 (m, 15H), 1.48 (s, 20H), 1.43 (s, 16H). $^{13}C$ NMR (100 MHz, $CDCl_3$) δ (ppm) 171.26, 171.09, 170.86, 166.93, 143.16, 129.46, 129.38, 129.10, 81.65, 80.81, 77.41, 77.09, 76.77, 69.45, 56.24, 56.10, 52.37, 52.08, 52.05, 49.32, 31.27, 29.73, 28.28, 28.22, 28.19, 28.09).

(2) The compound with a structure shown in formula A-2 (1.0 g, 1.3 mmol) obtained in step (1) was dissolved in a mixture of THF/methanol (10 mL, 1:1) to obtain a mixed solution, and lithium hydroxide (0.1 g, 4.0 mmol) was dissolved in 1 mL of water to obtain a lithium hydroxide aqueous solution; the lithium hydroxide aqueous solution was added to the mixed solution, and a resulting mixture was stirred at room temperature to allow an ester hydrolysis reaction for 12 h; and a product of the ester hydrolysis reaction was concentrated and diluted with 5 mL of water, a pH was adjusted with a 1 N hydrochloric acid solution to 7, and the solvent was removed through evaporation to obtain a first reaction precursor.

(3) HATU (1.0 g, 2.6 mmol) and 30 mL of DCM were added to the first reaction precursor obtained in step (2), and after the solids were completely dissolved, p-ethoxybenzylamine (0.4 g, 2.6 mmol) and DIPEA (0.3 g, 2.6 mmol) were added; a resulting mixture was stirred under nitrogen protection to allow a condensation reaction for 4 h, 70 mL of DCM was added to a product of the condensation reaction, and then the product was washed with water three times; and a resulting organic phase was dried, concentrated, and then purified through silica gel column chromatography to obtain a compound with a structure shown in formula A-3 (yield: 80%).

(4) 4 mL of TFA was added to the compound with a structure shown in formula A-3 (1.0 g, 1.1 mmol) obtained in step (3), and a resulting mixture was stirred at room temperature to allow a t-butyl ester group removal reaction for 12 h; and a product of the t-butyl ester group removal reaction was subjected to evaporation for TFA removal, and then separated and purified through RPLC to obtain a compound with a structure shown in formula A-4.

(5) The compound with a structure shown in formula A-4 (0.2 g, 0.3 mmol) obtained in step (4) and $GdCl_3 \cdot 6H_2O$ (111 mg, 0.3 mmol) were dissolved in 10 mL of water, a pH was adjusted with a 1 N sodium hydroxide solution to 7, a resulting reaction system was heated to 100° C. to allow a complexation reaction for 6 h, and a product of the complexation reaction was separated through RPLC to obtain the complex GdL1.

Example 2

A cyclic Gd (III) complex with a chemical structure shown in formula I was provided, where in formula I, R was H, R' was H, and R" was a compound of

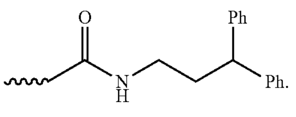

The cyclic Gd (III) complex in this example was denoted as complex GdL2.

A preparation method of the cyclic Gd (III) complex was as follows

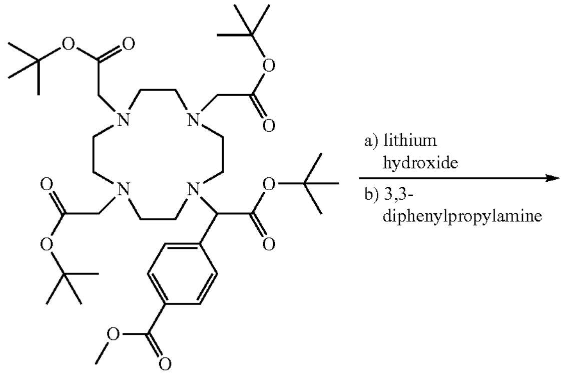

A-2

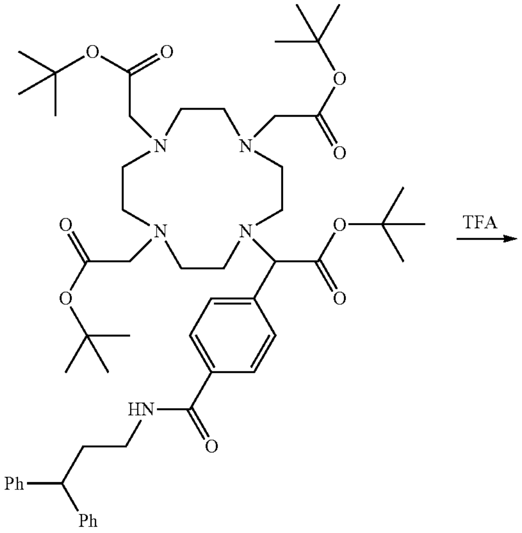

A-3

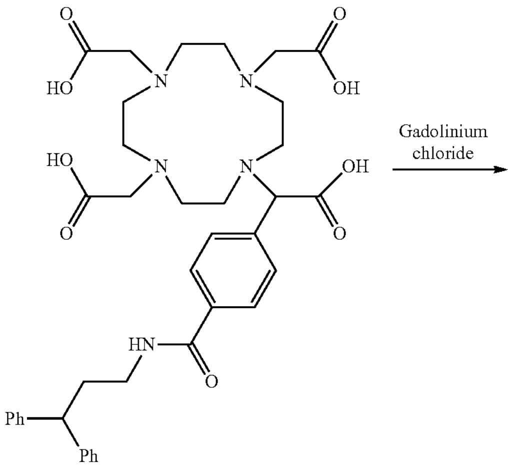

A-4

-continued

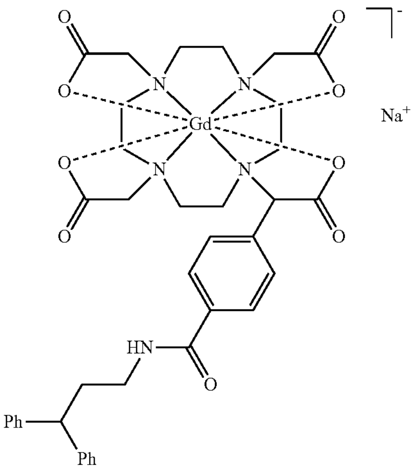

GdL2

R' = —H;

R'' =

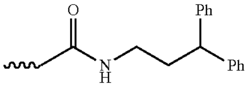

The complex GdL2 was prepared according to the preparation method in Example 1 (HPLC-MS (ESI$^-$) calculated for $C_{38}H_{43}GdN_5O_9$, [M]=871.23, found 871.25) except that, in step (2), 3,3-diphenylpropylamine was used instead of the p-ethoxybenzylamine.

Example 3

A cyclic Gd (III) complex with a chemical structure shown in formula I was provided, where in formula I, R was H, R' was H, and R'' was a compound of —$NO_2$. The cyclic Gd (III) complex in this example was denoted as complex GdL3.

A preparation method of the cyclic Gd (III) complex included the following steps:

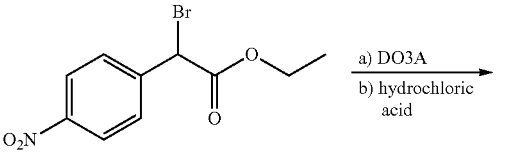

B-1

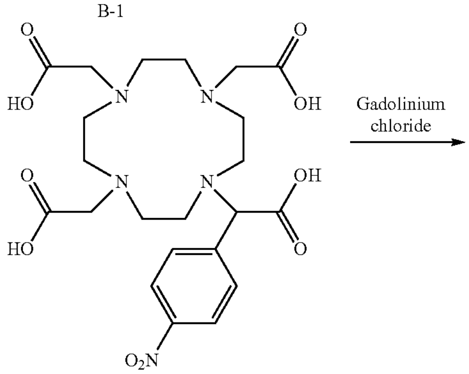

B-2

-continued

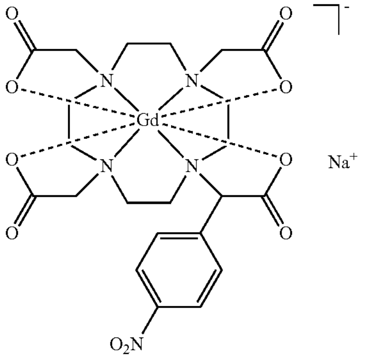

GdL3

R' = —H
R'' = —$NO_2$

S1. In a nitrogen atmosphere, a compound with a structure shown in formula B-1 (1.5 g, 5 mmol) was dissolved in 30 mL of acetonitrile, then DO3A (2.6 g, 5 mmol) and potassium carbonate (1.4 g, 10 mmol) were added, and a resulting mixture was heated to 70° C. and stirred to allow a nucleophilic substitution reaction for 17 h; and a product of the nucleophilic substitution reaction was subjected to concentration, filtration, evaporation to dryness, and concentration to obtain a second reaction precursor.

S2. The second reaction precursor obtained in S1 was added to 30 mL of a hydrochloric acid solution (6 N), and a resulting mixture was heated to 100° C. for reflux and continuously stirred to allow a t-butyl ester group removal reaction for 17 h; and a product of the t-butyl ester group removal reaction was separated and purified through reversed-phase semi-preparative liquid chromatography to obtain a compound with a structure shown in formula B-2 ($^1$H NMR (400 MHz, D2O) δ (ppm): 8.07 (d, 2H, J=8.52 Hz), 7.61 (d, 2H, J=8.52 Hz), 5.24 (s, 1H), 4.10-2.30 (m, 25H). $^{13}$C NMR (100 MHz, D2O) δ 178.85, 176.45, 175.50, 170.44, 170.16, 168.41, 147.19, 144.20, 131.10, 129.85, 124.52, 123.54, 65.54, 60.63, 57.00, 56.07, 55.16, 54.71, 54.05, 51.89, 51.68, 50.79, 49.94, 49.36, 48.31, 46.55, 45.83, 43.58, 42.51).

S3. The compound with a structure shown in formula B-2 (0.2 g, 0.4 mmol) obtained in S2 and $GdCl_3·6H_2O$ (148 mg, 0.4 mmol) were dissolved in 10 mL of water, a pH was adjusted with a 1 N sodium hydroxide solution to 7, and a resulting reaction system was heated to 100° C. to allow a complexation reaction for 6 h; and a product of the complexation reaction was separated through reversed-phase preparative liquid chromatography to obtain the complex GdL3 (HPLC-MS (ESI$^-$) calculated for $C_{22}H_{27}GdN_5O_{10}$ [M]$^-$ 679.10, found 679.12).

Example 4

A cyclic Gd (III) complex with a chemical structure shown in formula I was provided, where in formula I, R was H, R' was H, and R" was a compound of —H. The cyclic Gd (III) complex in this example was denoted as complex GdL4.

A preparation method of the cyclic Gd (III) complex was as follows

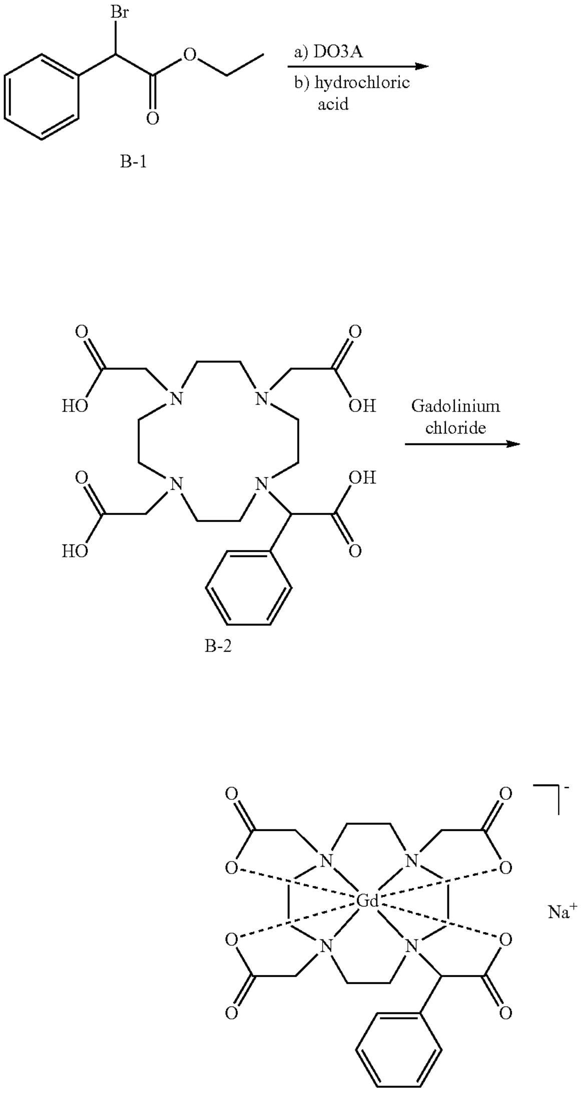

B-1

B-2

GdL4

R' = —H
R'' = —H

The complex GdL4 was prepared according to the preparation method in Example 3 (HPLC-MS (ESI) calculated for $C_{22}H_{28}GdN_4O_8$, [M]$^-$ 634.11, found 634.11) except that, in S 1, a compound with a chemical structure shown in formula B-1 in which R was H, R' was H, and R" was H was used as a raw material.

Example 5

A cyclic Gd (III) complex with a chemical structure shown in formula I was provided, where in formula I, R was H, R' was H, and R" was a compound of —OBn. The cyclic Gd (III) complex in this example was denoted as complex GdL5.

A preparation method of the cyclic Gd (III) complex was as follows

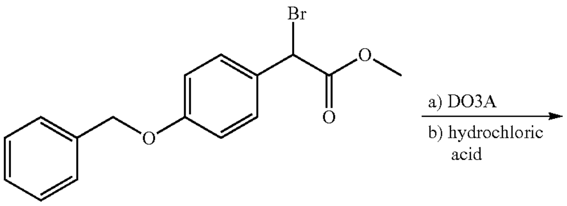

B-1

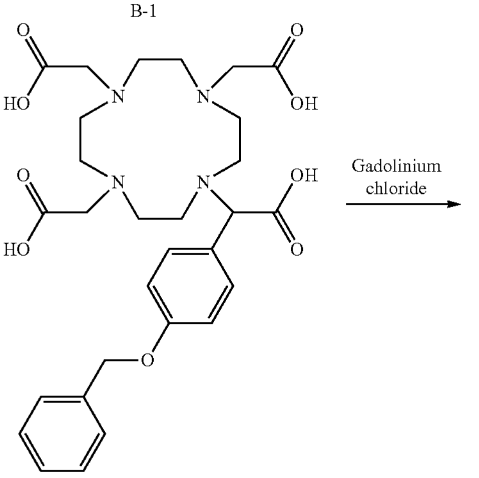

B-2

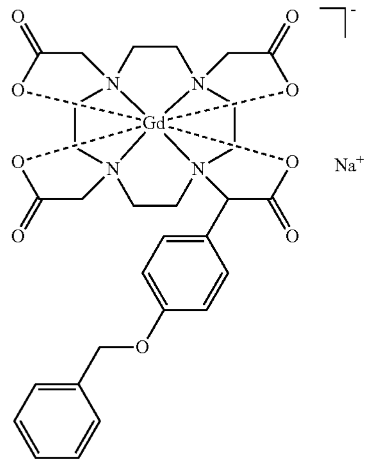

GdL5

R' = —H
R'' = —OBn

The complex GdL5 was prepared according to the preparation method in Example 3 (HPLC-MS (ESI$^-$) calculated for $C_{29}H_{34}GdN_4O_9$ $[M]^-$ 740.16, found 740.20) except that, in S1, a compound with a chemical structure shown in formula B-1 in which R was H, R' was H, and R" was a compound of —OBn was used as a raw material.

Example 6

A cyclic Gd (III) complex with a chemical structure shown in formula I was provided, where in formula I, R was H, R' was H, and R" was a compound of -Ph. The cyclic Gd (III) complex in this example was denoted as complex GdL6.

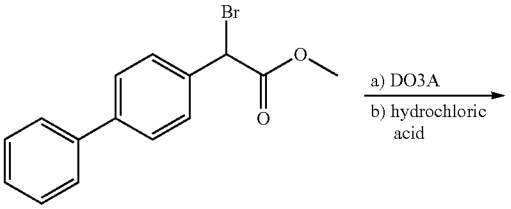

B-1

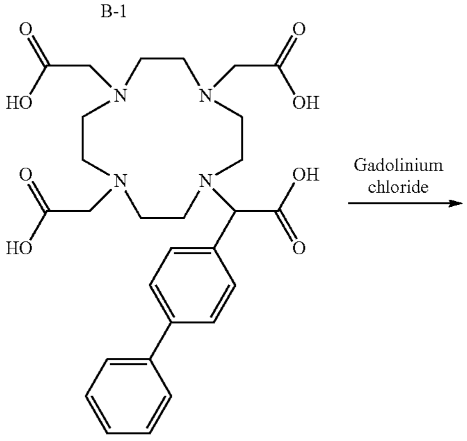

B-2

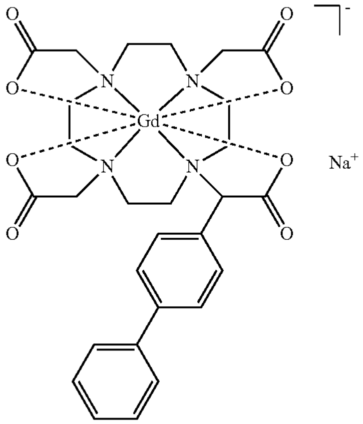

GdL6

R' = —H
R'' = —Ph

A preparation method of the cyclic Gd (III) complex was as follows

The complex GdL6 was prepared according to the preparation method in Example 3 (HPLC-MS (ESI$^-$) calculated for $C_{28}H_{32}GdN_4O_8$, $[M]^-$ 710.15, found 710.20) except that, in S1, a compound with a chemical structure shown in formula B-1 in which R was H, R' was H, and R" was a compound of -Ph was used as a raw material.

Example 7

A cyclic Gd (III) complex with a chemical structure shown in formula I was provided, where in formula I, R was H, R' was -Ph, and R" was a compound of H. The cyclic Gd (III) complex in this example was denoted as complex GdL7.

A preparation method of the cyclic Gd (III) complex was as follows

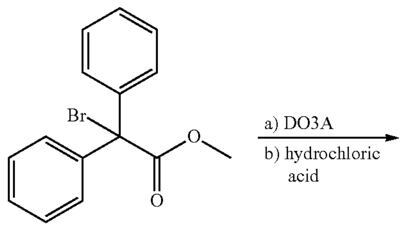

B-1

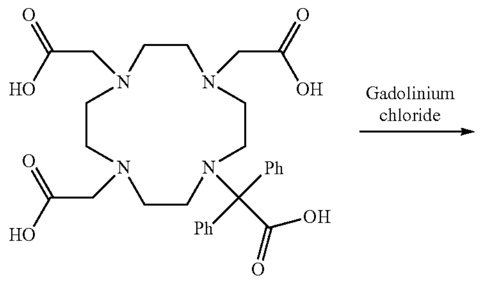

B-2

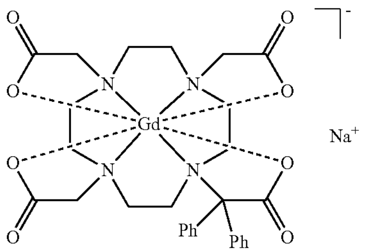

GdL7

R' = —Ph
R'' = —H

The complex GdL7 was prepared according to the preparation method in Example 3 (HPLC-MS ($ESI^-$) calculated for $C_{28}H_{32}GdN_4O_8$, $[M]^-$ 710.15, found 710.17) except that, in S1, a compound with a chemical structure shown in formula B-1 in which R was H, R' was H, and R'' was a compound of -Ph was used as a raw material.

Example 8

A cyclic Gd (III) complex with a chemical structure shown in formula I was provided, where in formula I, R was —$CH_2CH_3$, R' was H, and R'' was a compound of —COOH. The cyclic Gd (III) complex in this example was denoted as complex GdL8.

A preparation method of the cyclic Gd (III) complex included the following steps

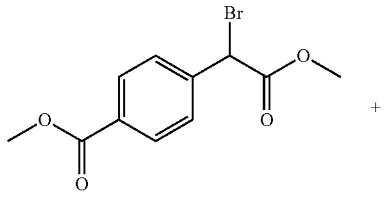

C-1

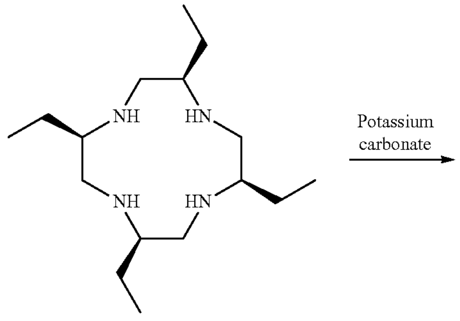

Chiral cyclen

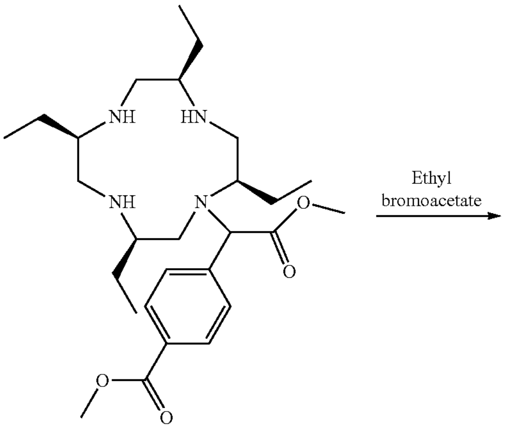

C-2

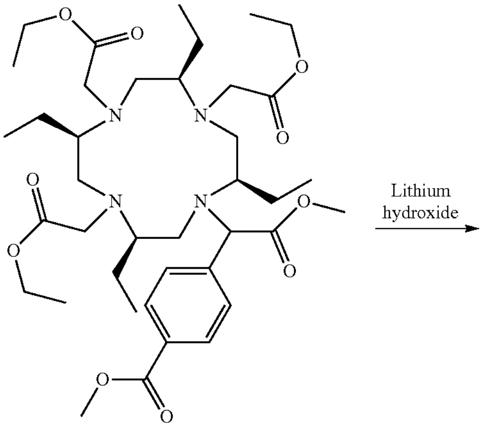

C-3

-continued

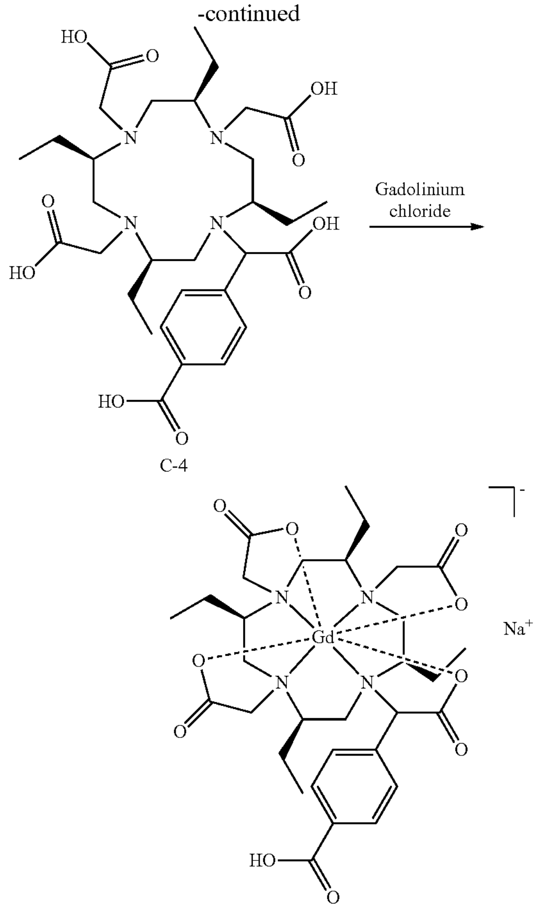

C-4

GdL8

R' = —H
R'' = —COOH (a) A compound C-1 (1.0 g, 3.5 mmol) and a compound with a structure shown in chiral cyclen (1.0 g, 3.5 mmol) were mixed and dissolved in 20 mL of acetonitrile, and a resulting solution was stirred at room temperature to allow a first nucleophilic substitution reaction for 18 h; a product of the first nucleophilic substitution reaction was subjected to evaporation for solvent removal and dissolved in 50 mL of ethyl acetate, a hydrochloric acid solution (1 N, 20 mL×3) was added, and resulting aqueous phases were separated, combined, and subjected to pH adjustment with potassium carbonate to 10; and DCM (30 mL×3) was added, and resulting organic phases were separated, combined, and subjected to evaporation to dryness to obtain a compound with a structure shown in formula C-2.

(b) In a nitrogen atmosphere, the compound with a structure shown in formula C-2 (1.0 g, 2 mmol) obtained in step (a) was dissolved in 20 mL of acetonitrile, then potassium carbonate (1.4 g, 10.2 mmol) and ethyl bromoacetate (1.7 g, 10.2 mmol) were successively added, and a resulting mixture was stirred to allow a second nucleophilic substitution reaction for 18 h; and a product of the second nucleophilic substitution reaction was subjected to filtration, concentration, and purification through silica gel column chromatography (ethyl acetate methanol=10:1) successively to obtain a compound with a structure shown in formula C-3.

[0310](c) The compound with a structure shown in formula C-3 (1.0 g, 1.3 mmol) obtained in step (b) was dissolved in a mixture of THF/methanol (10 mL, 1:1) to obtain a mixed solution, and lithium hydroxide (0.1 g, 4 mmol) was dissolved 1 mL of deionized water to obtain a lithium hydroxide aqueous solution; the lithium hydroxide aqueous solution was added to the mixed solution, and a resulting mixture was continuously stirred at room temperature to allow a hydrolysis reaction for 6 h; and a product of the hydrolysis reaction was subjected to concentration, then 10 mL of water was added, a pH was adjusted with a 1 N hydrochloric acid solution to 7, and purification was further conducted through RPLC to obtain a compound with a structure shown in formula C-4 ($^1$H NMR (400 MHz, D2O) δ (ppm): 7.82 (d, 2H, J=8.48 Hz), 7.30 (d, 2H, J=8.48 Hz), 4.78 (s, 1H), 4.20-3.62 (m, 7H), 3.41 (s, 2H), 3.32-3.10 (m, 6H), 2.89 (m, 6H), 2.58 (d, 1H, J=11.84 Hz), 2.20-1.82 (m, 4H), 1.37 (m, 3H), 1.10-0.65 (m, 12H), 0.47 (t, 3H, J=7.08 Hz), 0.24 (s, 1H)).

(d) The compound with a structure shown in formula C-4 (0.2 g, 0.3 mmol) obtained in step (c) and $GdCl_3·6H_2O$ (111 mg, 0.3 mmol) were dissolved in 10 mL of water, a pH was adjusted with a 1 N sodium hydroxide solution to 7, and a resulting reaction system was heated to 100° C. to allow a complexation reaction for 6 h; and a product of the complexation reaction was separated through reversed-phase preparative liquid chromatography to obtain the complex GdL9 (HPLC-MS (ESI$^-$) calculated for $C_{31}H_{44}GdN_4O_{10}$ $[M]^-$ 790.23, found 790.30).

Example 9

A cyclic Gd (III) complex with a chemical structure shown in formula I was provided, where in formula I, R was $—CH_2CH_3$, R' was H, and R'' was a compound of

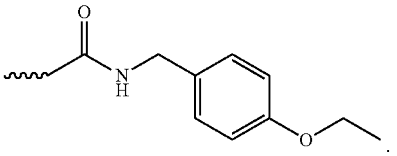

The cyclic Gd (III) complex in this example was denoted as complex GdL9.

A preparation method of the cyclic Gd (III) complex included the following steps

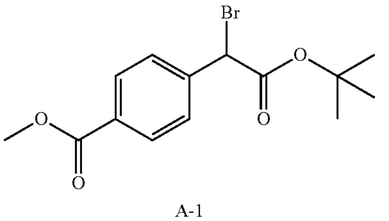

+

A-1

-continued

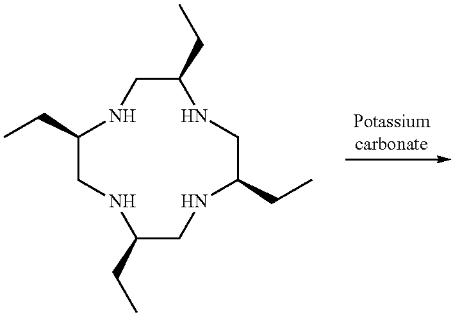

Chiral cyclen

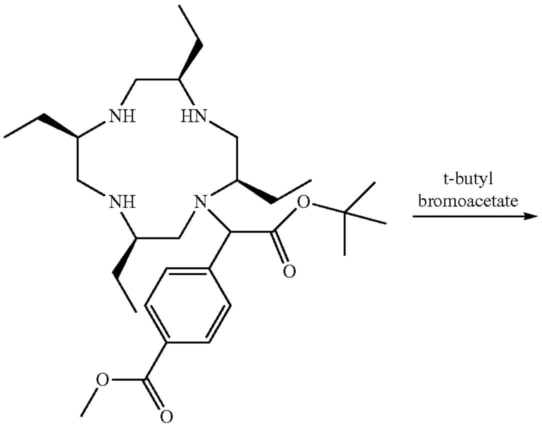

D-2

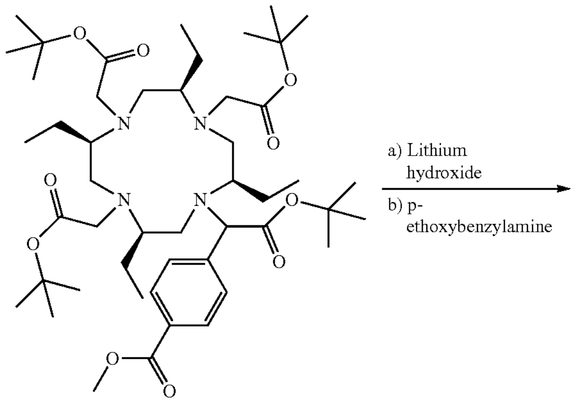

D-3

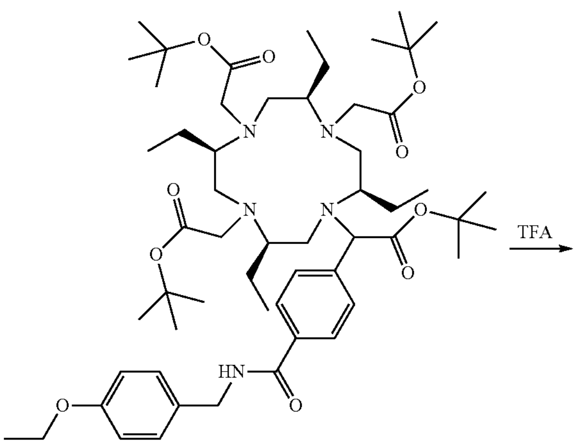

D-4

-continued

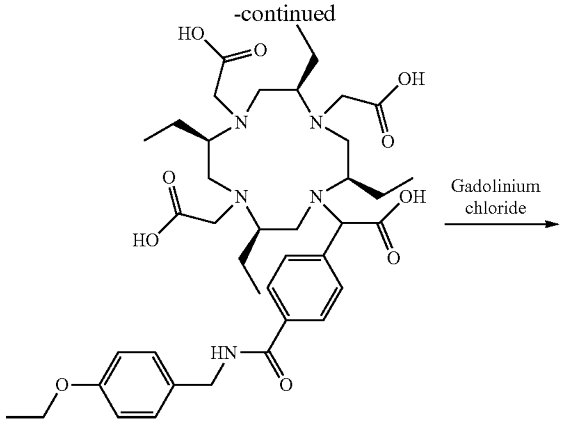

D-5

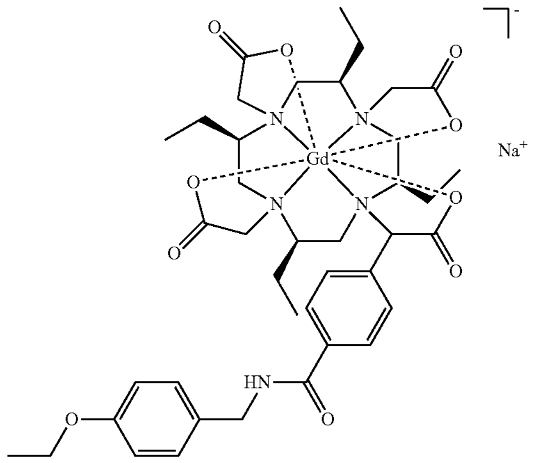

GdL9

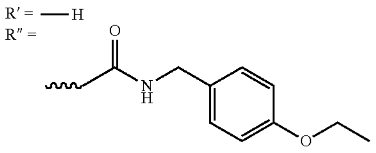

1) A compound with a structure shown in formula A-1 (1.0 g, 3 mmol) and a compound with a structure shown in chiral cyclen (0.9 g, 3 mmol) were dissolved in 30 mL of acetonitrile, and a resulting reaction solution was heated to 80° C. and continuously stirred in a nitrogen atmosphere to allow a first nucleophilic substitution reaction for 7 d; and a product of the first nucleophilic substitution reaction was concentrated and purified through silica gel column chromatography (ethyl acetate:methanol=5:1) to obtain a compound with a structure shown in formula D-2.

2) In a nitrogen atmosphere, the compound with a structure shown in formula D-2 (1.6 g, 3 mmol) obtained in step 1), potassium carbonate (2.1 g, 15 mmol), and tert-butyl bromoacetate (2.9 g, 15 mmol) were dissolved in 20 mL of acetonitrile, and a resulting solution was stirred to allow a second nucleophilic substitution reaction for 18 h; and a product of the second nucleophilic substitution reaction was subjected to filtration, concentration, and purification through silica gel column chromatography (ethyl acetate:methanol=20:1) to obtain a compound with a structure shown in formula D-3 ($^1$H NMR (400 MHz, $CDCl_3$) δ (ppm): 7.95 (d, 2H, J=7.92 Hz), 7.46 (d, 2H, J=7.92 Hz), 4.51 (s, 1H), 3.21-2.69 (m, 14H), 2.37 (m, 1H), 2.20 (m, 2H), 1.80 (m, 1H), 1.72-1.10 (m, 51H), 1.01-0.75 (m, 14H). $^{13}C$ NMR (100 MHz, $CDCl_3$) δ(ppm) 172.62, 171.90, 171.75, 166.70, 143.16, 129.99, 129.31, 129.21, 80.85, 80.25, 80.08, 79.79, 77.51, 77.19, 76.87, 63.29, 60.24, 57.50, 56.92, 56.58, 56.10, 54.03, 53.40, 52.68, 52.41, 51.89, 51.75, 51.49, 50.89, 47.08, 31.85, 29.62, 29.59, 29.28, 28.03, 27.95, 27.83, 27.14, 23.65, 23.11, 23.00, 22.73, 22.62, 20.92, 14.14, 14.07, 12.26, 11.92, 11.70, 11.63).

3) The compound with a structure shown in formula D-3 (1.0 g, 1.7 mmol) obtained in step 2) was dissolved in a mixture of THF/methanol (10 mL, 1:1) to obtain a mixed solution, and lithium hydroxide (122 mg, 5.1 mmol) was dissolved in 1 mL of water to obtain a lithium hydroxide aqueous solution; the lithium hydroxide aqueous solution was added to the mixed solution, and a resulting mixture was stirred at room temperature to allow an ester hydrolysis reaction for 6 h; and a product of the ester hydrolysis reaction was concentrated, 10 mL of water was added, a pH was adjusted to 7 with a 1 N hydrochloric acid solution, and the solvent was removed through evaporation to obtain a third reaction precursor.

4) In a nitrogen atmosphere, the third reaction precursor obtained in step 3) was mixed with 20 mL of DCM, then HATU (1.3 g, 3.4 mmol), p-ethoxybenzylamine (0.5 g, 3.4 mmol), and DIPEA (0.4 g, 3.4 mmol) were successively added, and a resulting mixture was stirred at room temperature to allow a condensation reaction for 4 h; and a product of the condensation reaction was subjected to evaporation to dryness and then purified through silica gel column chromatography (ethyl acetate:methanol=10:1) to obtain a compound with a structure shown in formula D-4.

5) In a nitrogen atmosphere, the compound with a structure shown in formula D-4 (1.0 g, 1.0 mmol) obtained in step 4) was dissolved in 4 mL of TFA, and a resulting solution was stirred at room temperature under nitrogen protection to allow a t-butyl ester group removal reaction for 12 h; and a product of the t-butyl ester group removal reaction was concentrated and then separated and purified through reversed-phase preparative high-performance liquid chromatography to obtain a compound with a structure shown in formula D-5.

6) The compound with a structure shown in formula D-5 (0.3 g, 0.4 mmol) obtained in step 5) and $GdCl_3·6H_2O$ (148 mg, 0.4 mmol) were dissolved in 10 mL of water, a pH was adjusted with a 1 N sodium hydroxide solution to 7, a resulting reaction system was heated to 100° C. to allow a continuous complexation reaction for 6 h, and a product of the complexation reaction was separated through reversed-phase preparative high-performance liquid chromatography to obtain the complex GdL9.

Example 10

A cyclic Gd (III) complex with a chemical structure shown in formula I was provided, where in formula I, R was $—CH_2CH_3$, R' was H, and R" was a compound of $—NO_2$. The cyclic Gd (III) complex in this example was denoted as complex GdL10.

A preparation method of the cyclic Gd (III) complex included the following steps

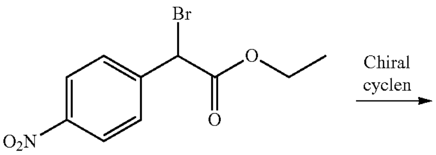

E-1

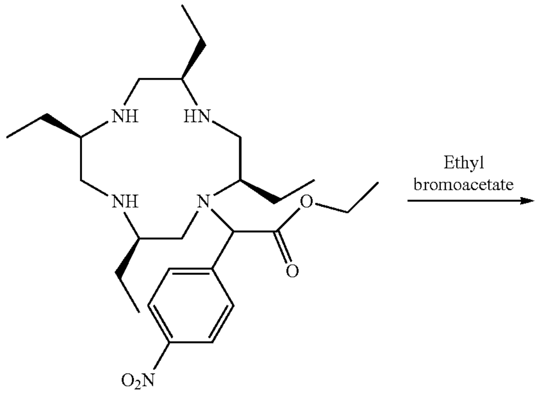

E-2

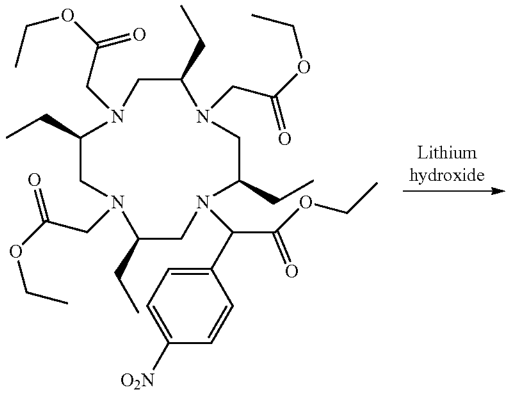

E-3

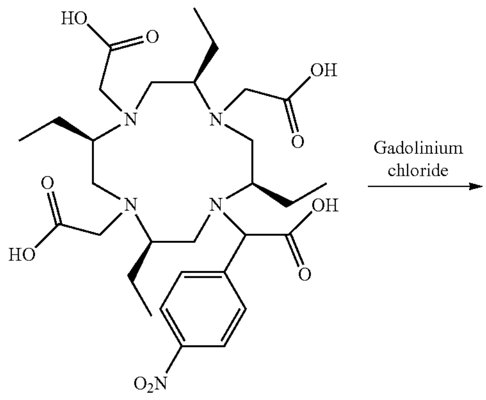

E-4

-continued

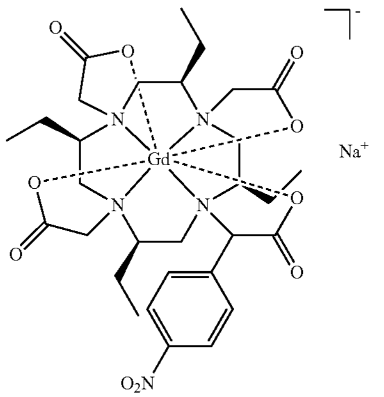

GdL10

R' = —H
R" = —$NO_2$ (1') In a nitrogen atmosphere, a compound with a structure shown in formula E-1 (1.0 g, 3.5 mmol) was dissolved in 20 mL of acetonitrile, then a compound with a structure shown in chiral cyclen (1.0 g, 3.5 mmol) was added, and a resulting mixture was stirred at room temperature to allow a first nucleophilic substitution reaction for 18 h; and a product of the first nucleophilic substitution reaction was concentrated and then purified through silica gel column chromatography (ethyl acetate:methanol=5:1) to obtain a compound with a structure shown in formula E-2 (yield: 81%).

(2') In a nitrogen atmosphere, the compound with a structure shown in formula E-2 (1.0 g, 2.0 mmol) obtained in step (1'), potassium carbonate (1.4 g, 10 mmol), and ethyl bromoacetate (1.7 g, 10 mmol) were dissolved in 20 mL of acetonitrile, and a resulting solution was stirred at room temperature to allow a second nucleophilic substitution reaction for 18 h; and a product of the second nucleophilic substitution reaction was subjected to filtration, concentration, and purification through silica gel column chromatography (ethyl acetate methanol=10:1) to obtain a compound with a structure shown in formula E-3 (yield: 73%, $^1$H NMR (400 MHz, D2O) δ (ppm): 7.97 (m, 2H), 7.31 (m, 2H), 5.25 (s, 1H), 4.35-2.31 (m, 16H), 2.05-0.08 (m, 20H). $^{13}$C NMR (100 MHz, D2O) δ(ppm): 189.90, 189.09, 178.06, 175.74, 175.36, 174.73, 174.28, 173.69, 173.17, 171.01, 168.59, 168.42, 168.36, 166.80, 166.51, 166.44, 164.94, 164.30, 153.96, 147.63, 147.56, 147.21, 141.00, 131.88, 131.23, 129.57, 124.48, 123.85, 118.82, 63.04, 62.69, 62.47, 61.24, 60.88, 59.70, 58.82, 57.61, 55.30, 52.43, 51.54, 51.22, 48.96, 48.21, 47.62, 44.23, 42.10, 20.65, 18.49, 18.04, 13.10, 12.76, 11.56, 11.12, 10.66, 10.20, 10.12, 9.91, 9.80, 9.70. HPLC-MS (ESI$^-$) Calculated for $C_{30}H_{48}N_5O_{10}$ $[M+H]^+$ 638.33, found 638.37).

(3') The compound with a structure shown in formula E-3 (1.0 g, 1.3 mmol) obtained in step (2') was dissolved in a mixture of THF/methanol (10 mL, 1:1) to obtain a mixed solution, and lithium hydroxide (0.1 g, 4 mmol) was dissolved in 1 mL of deionized water to obtain a lithium hydroxide aqueous solution; the lithium hydroxide aqueous solution was added to the mixed solution, and a resulting mixture was continuously stirred at room temperature to allow an ester hydrolysis reaction for 6 h; and a product of the ester hydrolysis reaction was concentrated, 10 mL of water was added, a pH was adjusted to 7 with a 1 N hydrochloric acid solution, and purification was conducted through reversed-phase preparative high-performance liquid chromatography to obtain a compound with a structure shown in formula E-4.

(4') The compound with a structure shown in formula E-4 obtained in step (3') and $GdCl_3·6H_2O$ (111 mg, 0.3 mmol) were dissolved in 10 mL of water, a pH was adjusted with a 1 N sodium hydroxide solution to 7, and a resulting reaction system was heated to 100° C. to allow a complexation reaction for 6 h; and a product of the complexation reaction was separated through reversed-phase preparative liquid chromatography to obtain the complex GdL10 (HPLC-MS (ESI$^-$) Calculated for $C_{30}H_{43}GdN_5O_{10}$ $[M]^-$ 719.23, found 719.21).

Example 11

A cyclic Gd (III) complex with a chemical structure shown in formula I was provided, where in formula I, R was —$CH_2CH_3$, R' was H, and R" was a compound of —$C(CH_3)_3$. The cyclic Gd (III) complex in this example was denoted as complex GdL11.

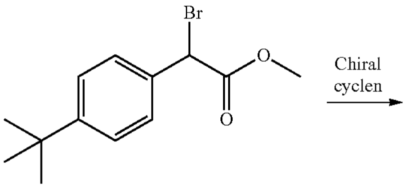

E-1

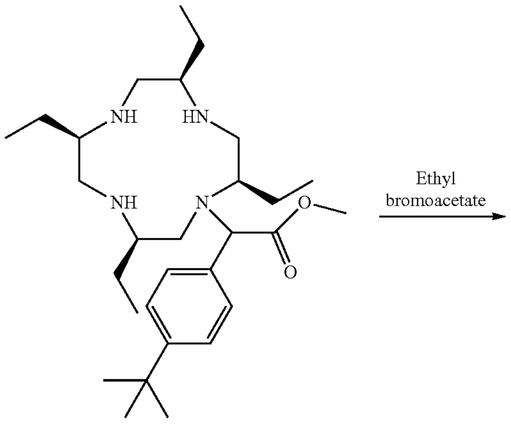

E-2

-continued

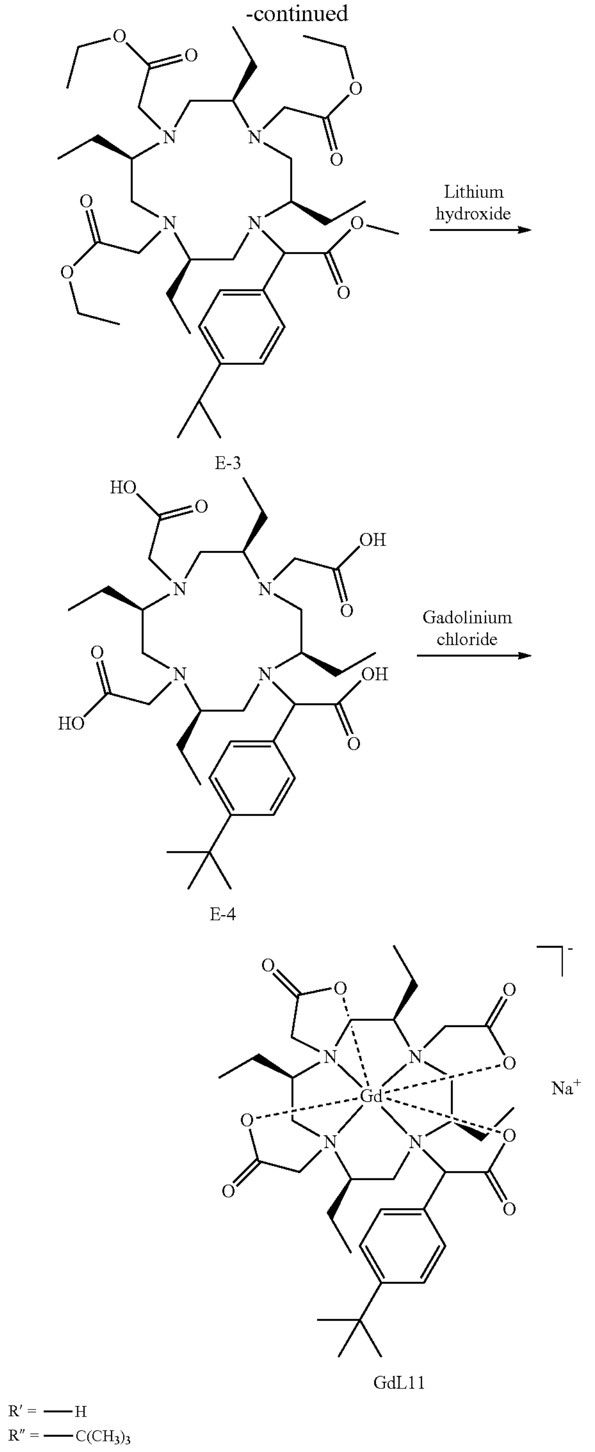

E-3

E-4

GdL11

A preparation method of the cyclic Gd (III) complex was as follows

The complex GdL11 was prepared according to the preparation method in Example 10 (HPLC-MS ($ESI^-$) Calculated for $C_{34}H_{52}GdN_4O_8$ [M]802.30, found 802.33) except that, in step (1'), a compound with a chemical structure shown in formula E-1 in which R" was —$C(CH_3)_3$ was used as a starting material.

Example 12

A cyclic Gd (III) complex with a chemical structure shown in formula I was provided, where in formula I, R was —$CH_2CH_3$, R' was H, and R" was a compound of —$CF_3$. The cyclic Gd (III) complex in this example was denoted as complex GdL12.

A preparation method of the cyclic Gd (III) complex was as follows

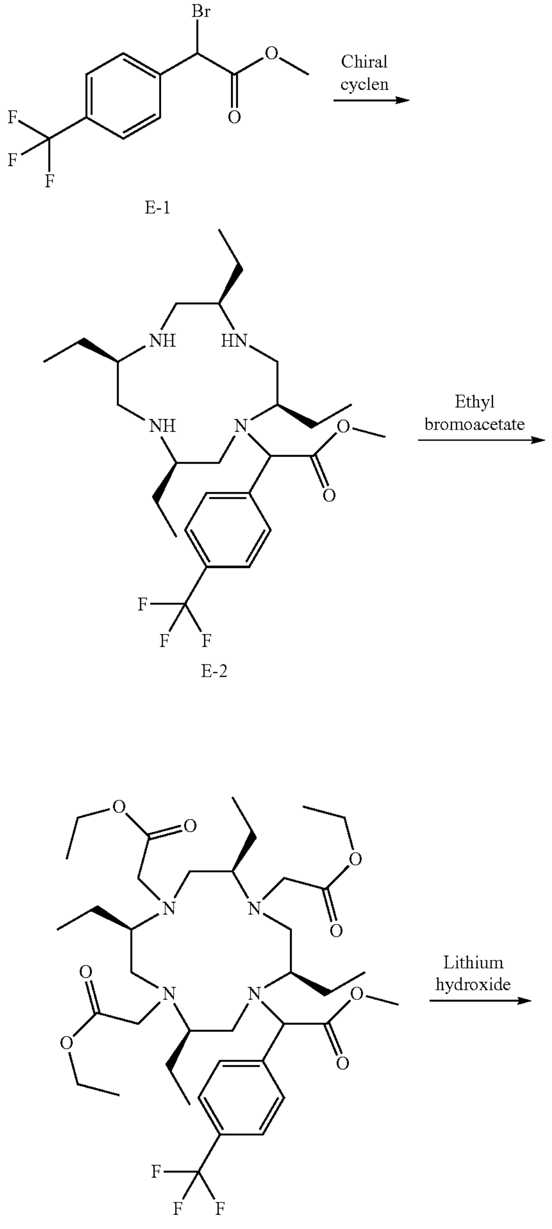

E-1

E-2

E-3

-continued

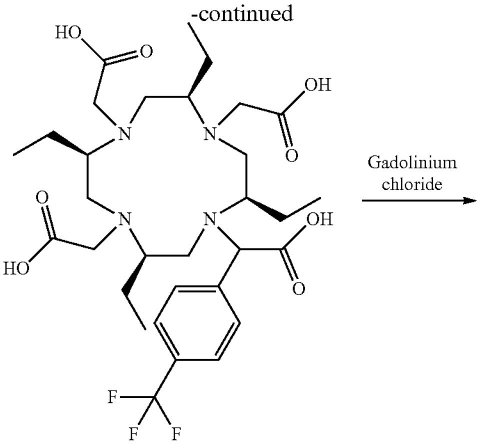

E-4

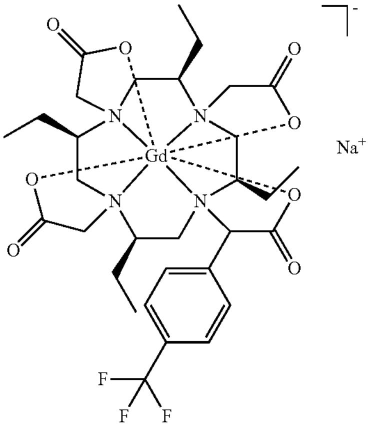

GdL12

R′ = —H
R″ = —$CF_3$

The complex GdL12 was prepared according to the preparation method in Example 10 (HPLC-MS ($ESI^-$) Calculated for $C_{31}H_{43}F_3GdN_4O_8$ $[M]^-$: 814.23, found 814.25) except that, in step (1'), a compound with a chemical structure shown in formula E-1 in which R" was —$CF_3$ was used as a starting material.

Test 1:1.5 T, 3 T, and 7 T NMR instruments were used to detect relaxation rate parameters of some complexes, and results were shown in Table 1.

TABLE 1

Relaxation rate parameters of the complexes GdL3, GdL4, GdL9, and GdL10

| | $r_1$ ($mM^{-1}$ $s^{-1}$, 1.5 T) | $r_1$ ($mM^{-1}$ $s^{-1}$, 3 T) | $r_1$ ($mM^{-1}$ $s^{-1}$, 7 T) |
|---|---|---|---|
| GdL4 | 5.35 | 4.22 | — |
| GdL3 | 5.09 | 4.18 | — |
| GdL10 | 7.00 | 5.88 | — |
| GdL9 | 8.23 | 7.20 | 5.39 |

It can be seen from Table 1 that the cyclic Gd (III) complex provided by the present disclosure has the optimal relaxation rate range for MRI, where GdL9 has a relaxation rate suitable for high-field MRI.

Test 2: The performance of a complex as an MRI contrast agent targeting the liver and gallbladder was tested.

FIG. 1 shows hepatobiliary MRI images obtained when the complex GdL1 prepared in Example 1 is used as a liver and gallbladder-targeted MRI contrast agent to detect the liver and gallbladder of mice at 0 min, 5 min, 10 min, 20 min, 30 min, 1 h, and 2 h after the mice are administered with GdL1, and it can be seen from FIG. 1 that the complex GdL1 can target the liver and gallbladder.

Figure 2:
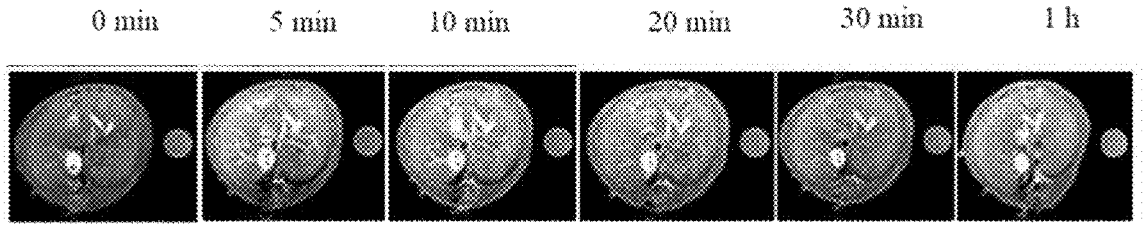
FIG. 2 shows hepatobiliary MRI images obtained when the complex GdL3 prepared in Example 3 of the present disclosure is used as a liver and gallbladder-targeted MRI contrast agent to detect the liver and gallbladder of mice at 0 min, 5 min, 10 min, 20 min, 30 min, and 1 h after the mice are administered with GdL3.

FIG. 2 shows hepatobiliary MRI images obtained when the complex GdL3 prepared in Example 3 is used as a liver and gallbladder-targeted MRI contrast agent to detect the liver and gallbladder of mice at 0 min, 5 min, 10 min, 20 min, 30 min, and 1 h after the mice are administered with GdL3, and it can be seen from FIG. 2 that the complex GdL3 shows excellent targetability to the liver and gallbladder and thus is suitable for hepatobiliary imaging.

Figure 3:
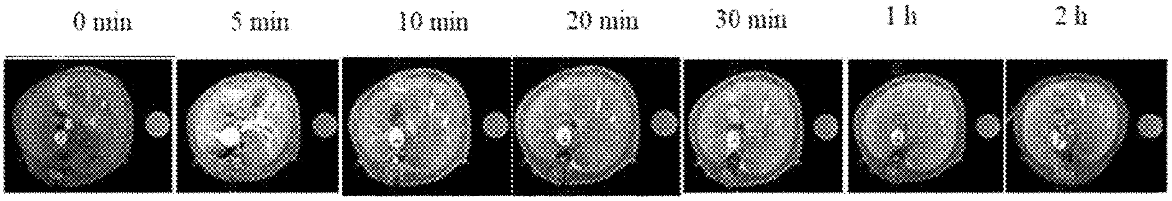
FIG. 3 shows hepatobiliary MRI images obtained when the complex GdL4 prepared in Example 4 of the present disclosure is used as a liver and gallbladder-targeted MRI contrast agent to detect the liver and gallbladder of mice at 0 min, 5 min, 10 min, 20 min, 30 min, 1 h, and 2 h after the mice are administered with GdL4.

FIG. 3 shows hepatobiliary MRI images obtained when the complex GdL4 prepared in Example 4 is used as a liver and gallbladder-targeted MRI contrast agent to detect the liver and gallbladder of mice at 0 min, 5 min, 10 min, 20 min, 30 min, 1 h, and 2 h after the mice are administered with GdL4, and it can be seen from FIG. 3 that the complex GdL4 shows excellent targetability to the liver and gallbladder and thus is suitable for hepatobiliary imaging.

Figure 4:
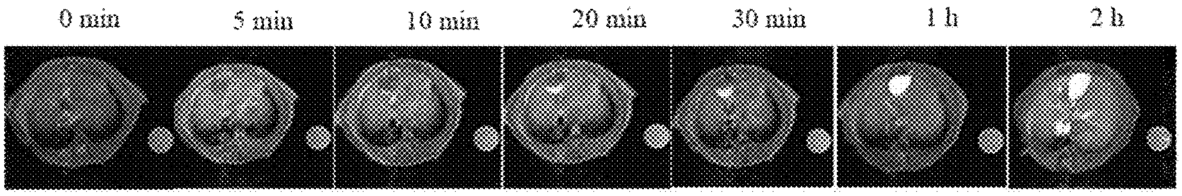
FIG. 4 shows hepatobiliary MRI images obtained when the complex GdL8 prepared in Example 8 of the present disclosure is used as a liver and gallbladder-targeted MRI contrast agent to detect the liver and gallbladder of mice at 0 min, 5 min, 10 min, 20 min, 30 min, 1 h, and 2 h after the mice are administered with GdL8.

FIG. 4 shows hepatobiliary MRI images obtained when the complex GdL8 prepared in Example 8 is used as a liver and gallbladder-targeted MRI contrast agent to detect the liver and gallbladder of mice at 0 min, 5 min, 10 min, 20 min, 30 min, 1 h, and 2 h after the mice are administered with GdL8, and it can be seen from FIG. 4 that the complex GdL8 can target the liver and gallbladder.

Figure 5:
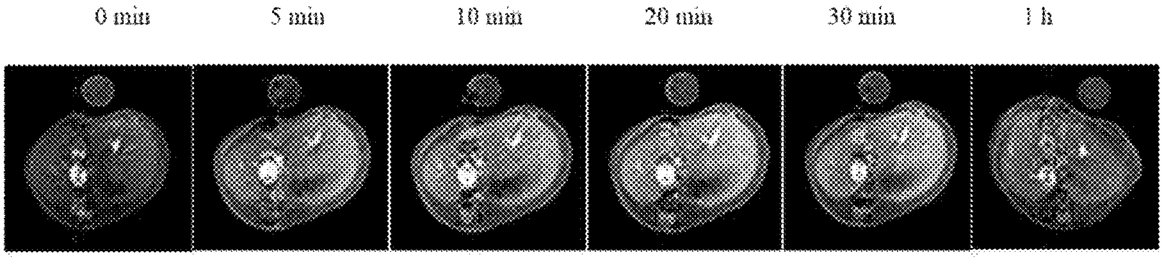
FIG. 5 shows hepatobiliary MRI images obtained when the complex GdL9 prepared in Example 9 of the present disclosure is used as a liver and gallbladder-targeted MRI contrast agent to detect the liver and gallbladder of mice at 0 min, 5 min, 10 min, 20 min, 30 min, and 1 h after the mice are administered with GdL9.

FIG. 5 shows hepatobiliary MRI images obtained when the complex GdL9 prepared in Example 9 is used as a liver and gallbladder-targeted MRI contrast agent to detect the liver and gallbladder of mice at 0 min, 5 min, 10 min, 20 min, 30 min, and 1 h after the mice are administered with GdL9, and it can be seen from FIG. 5 that the complex GdL9 can target the liver and gallbladder.

Figure 6:
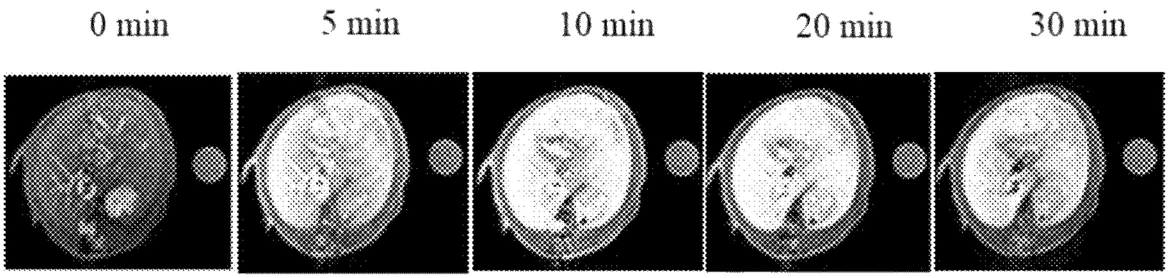
FIG. 6 shows hepatobiliary MRI images obtained when the complex GdL10 prepared in Example 10 of the present disclosure is used as a liver and gallbladder-targeted MRI contrast agent to detect the liver and gallbladder of mice at 0 min, 5 min, 10 min, 20 min, and 30 min after the mice are administered with GdL10.

FIG. 6 shows hepatobiliary MRI images obtained when the complex GdL10 prepared in Example 10 is used as a liver and gallbladder-targeted MRI contrast agent to detect the liver and gallbladder of mice at 0 min, 5 min, 10 min, 20 min, and 30 min after the mice are administered with GdL10, and it can be seen from FIG. 6 that the complex GdL10 shows extremely-excellent targetability to the liver and gallbladder and can lead to an extremely-excellent imaging effect.

Test 3: The stability of some complexes was tested.

The stability of a compound in a pH 1 acidic solution was tested through high-performance liquid chromatography (HPLC). GdL2, GdL9, and GdL10 were each dissolved in a pH 1 acidic solution and placed at room temperature (298 K, 25° C.), then the decay of each of the above compounds over time was tested through HPLC, and a half-life time ($t_{1/2}$) was calculated. The half-life times of Primovist and Gd-DOTA were reported in references.

TABLE 2

Stability of the complexes GdL2, GdL9, and GdL10

| Compound | Primovist | Gd-DOTA | GdL2 | GdL9 | GdL10 |
|---|---|---|---|---|---|
| Half-life time | <5 s | 14 d | 20 d | >1 year | >1 year |

It can be seen from Table 2 that the cyclic Gd (III) complex provided by the present disclosure exhibits excellent targetability to the liver and gallbladder and high stability; and after the chiral group R is introduced, the stability of the cyclic Gd (III) complex is greatly improved (which is significantly higher than that of Primovist and Gd-DOTA), where the release of metal ions is not detected in GdL9 and GdL10 within 1 year, indicating excellent stability.

It can be known from the examples that the cyclic Gd (III) complex provided by the present disclosure has the optimal relaxation rate range for MRI, where GdL9 has a relaxation rate suitable for high-field MRI; the cyclic Gd (III) complex has high stability, which is significantly higher than that of Primovist and Gd-DOTA; and after the chiral group R is introduced, the stability of the cyclic Gd (III) complex is greatly improved, where the release of metal ions is not detected in GdL9 and GdL10 within 1 year, indicating excellent stability.

The above description of examples is merely provided to help illustrate the method of the present disclosure and a core idea thereof. It should be noted that several improvements and modifications may be made by persons of ordinary skill in the art without departing from the principle of the present disclosure, and these improvements and modifications should also fall within the protection scope of the present disclosure. Various modifications to these examples are apparent to those of professional skill in the art, and the general principles defined herein may be implemented in other examples without departing from the spirit or scope of the present disclosure. Thus, the present disclosure is not limited to the examples shown herein, but falls within the widest scope consistent with the principles and novel features disclosed herein.

What is claimed is:

1. A cyclic Gd (III) complex with a chemical structure shown in formula I:

formula I

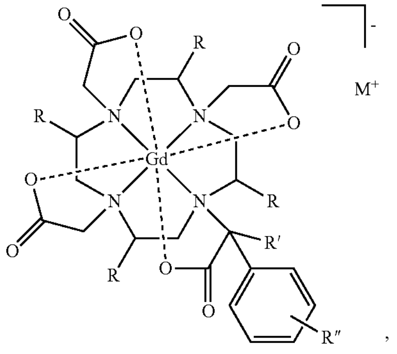

, wherein R in formula I is selected from the group consisting of $C_2$-$C_4$ alkyl, —$CH_2OH$, —$CH(CH_3)OH$, —$CH_2CH_2OH$, —$CH_2Ph$, —$(CH_2)_2Ph$, —$(CH_2)_3Ph$, —$(CH_2)_3NH_2$, and —$(CH_2)_4Ph$, and R in formula I has a configuration independently of S or R R" in formula I is at an ortho, meta, or para position of a benzene ring;

R' and R" in formula I are each independently selected from the group consisting of H, $C_1$-$C_{10}$ alkyl, fluorine, chlorine, bromine, iodine, —$CF_3$, —$CCl_3$, —$CBr_3$, $C_1$-$C_{10}$ alkoxy, —COOH, —$R_1$COOH, —$COOR_1$, -Ph, —$NO_2$, substituted phenyl, —$R_1$-Ph, —$R_1NO_2$, —$OR_1$-Ph, —$CONHR_3$,

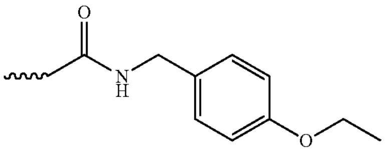

,

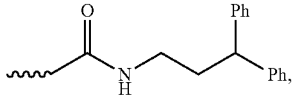

, $R_1$ in each of —$R_1$COOH, —$COOR_1$, —$R_1$-Ph, —$R_1NO_2$, and —$OR_1$-Ph is independently $C_1$-$C_5$ alkyl;

a substituent on the substituted phenyl is selected from the group consisting of $C_1$-$C_5$ alkyl, fluorine, chlorine, bromine, iodine, —$CF_3$, —$CCl_3$, —$CBr_3$, $C_1$-$C_5$ alkoxy, —COOH, —$R_2$COOH, —$COOR_2$, -Ph, —$R_2NO_2$, —$OR_2$-Ph, —$CONHR_2$, —$SO_2$—$R_2$, and —SO—$R_2$, and $R_2$ in each of —$R_2$COOH, —$COOR_2$, -Ph, —$R_2NO_2$, —$OR_2$-Ph, —$CONHR_2$, —$SO_2$—$R_2$, and —SO—$R_2$ is independently $C_1$-$C_3$ alkyl;

$R_3$, $R_4$, and $R_5$ respectively in —$CONHR_3$, —$SO_2$—$R_4$, and —SO—$R_5$ are each independently $C_1$-$C_5$ alkyl or benzyl; and $M^+$ in formula I is a metal cation or a glucosamine cation.

2. The cyclic Gd (III) complex according to claim 1, wherein R in formula I is selected from the group consisting of —$CH_2CH_3$, —$CH(CH_3)_2$, —$CH(CH_3)OH$, —$CH_2Ph$, and —$(CH_2)_4Ph$ R' and R" in formula I are each independently selected from the group consisting of H, —COOH, $CONHR_3$, —$CF_3$, —$C(CH_3)_3$, -Ph, —$NO_2$, —OBn,

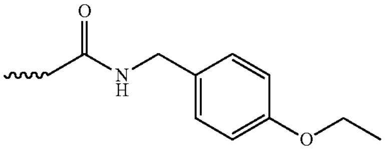

,

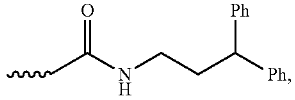

,

—$SO_2$—$R_4$, and —SO—$R_5$; and $R_3$, $R_4$, and $R_5$ respectively in —$CONHR_3$, —$SO_2$—$R_4$, and —SO—$R_5$ are each independently $C_1$-$C_5$ alkyl or benzyl.

3. The cyclic Gd (III) complex according to claim 1, wherein $M^+$ in formula I is selected from the group consisting of $Na^+$, $K^+$, $Li^+$, and a glucosamine cation.

4. A preparation method of the cyclic Gd (III) complex according to claim 1, wherein in formula I, R is selected from the group consisting of $C_2$-$C_4$ alkyl, —$CH_2OH$, —$CH(CH_3)OH$, —$CH_2CH_2OH$, —$CH_2Ph$, —$(CH_2)_2Ph$, —$(CH_2)_3Ph$, —$(CH_2)_3NH_2$, and —$(CH_2)_4Ph$ R' is H, and R" is

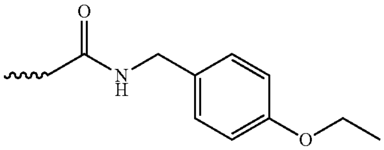

or

-continued

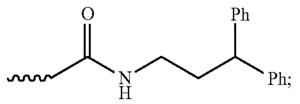

and the preparation method comprises the following steps:

1) mixing a compound with a structure shown in formula A-1, a compound with a structure shown in chiral cyclen, and acetonitrile to allow a first nucleophilic substitution reaction to obtain a compound with a structure shown in formula D-2;

2) in a nitrogen atmosphere, mixing the compound with a structure shown in formula D-2 obtained in step 1), acetonitrile, potassium carbonate, and tert-butyl bromoacetate to allow a second nucleophilic substitution reaction to obtain a compound with a structure shown in formula D-3;

3) mixing the compound with a structure shown in formula D-3 obtained in step 2), THF, methanol, and a lithium hydroxide aqueous solution to allow an ester hydrolysis reaction to obtain a third reaction precursor;

4) in a nitrogen atmosphere, mixing the third reaction precursor obtained in step 3) with HATU, DCM, an amine compound, and DIPEA to allow a condensation reaction to obtain a compound with a structure shown in formula D-4;

5) in a nitrogen atmosphere, mixing the compound with a structure shown in formula D-4 obtained in step 4) and TFA to allow a t-butyl ester group removal reaction to obtain a compound with a structure shown in formula D-5; and 6) mixing the compound with a structure shown in formula D-5 obtained in step 5), a gadolinium source, water, and an $M^+$-containing solution to allow a complexation reaction to obtain the cyclic Gd (III) complex, wherein the $M^+$-containing solution in step 6) is a solution of a metal hydroxide or a glucosamine,

A-1

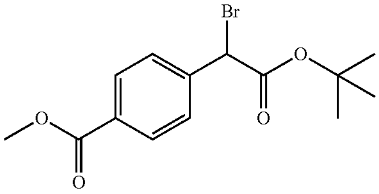

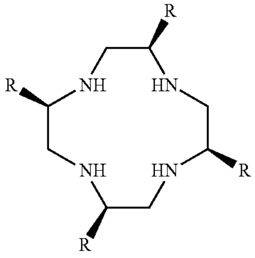

Chiral cyclen

-continued

D-2

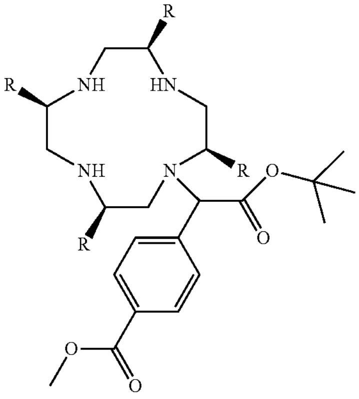

D-3

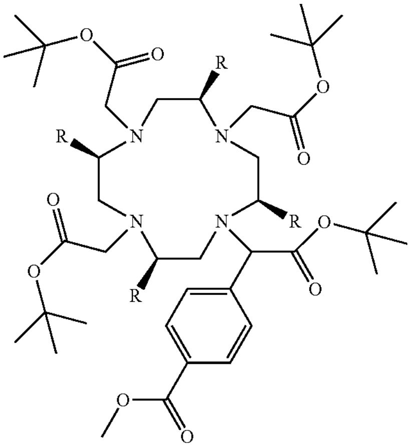

D-4

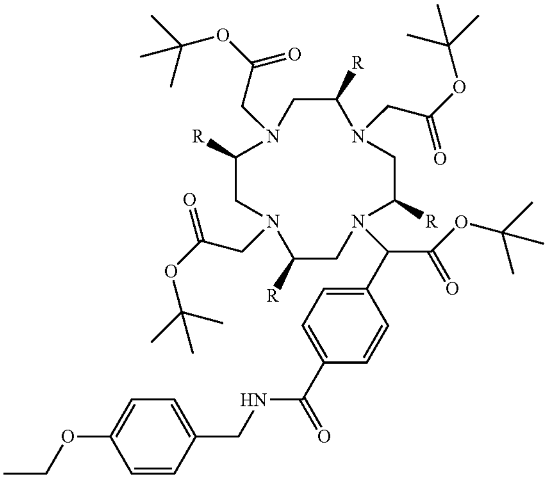

-continued

D-5

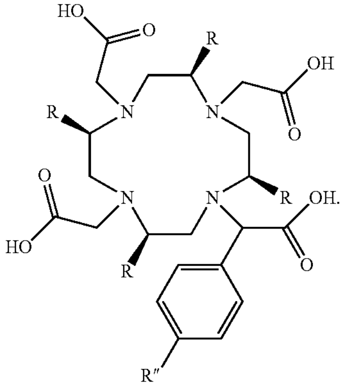

5. The preparation method according to claim 4, wherein R in formula I is selected from the group consisting of $—CH_2CH_3$, $—CH(CH_3)_2$, $—CH(CH_3)OH$, $—CH_2Ph$, and $—(CH_2)_4Ph$.

6. The preparation method according to claim 4, wherein $M^+$ in formula I is selected from the group consisting of $Na^+$, $K^+$, $Li^+$, and a glucosamine cation.

7. The preparation method according to claim 4, wherein the ester hydrolysis reaction in step 3) is conducted at room temperature for 4 h to 8 h.

8. The preparation method according to claim 5, wherein the ester hydrolysis reaction in step 3) is conducted at room temperature for 4 h to 8 h.

9. The preparation method according to claim 6, wherein the ester hydrolysis reaction in step 3) is conducted at room temperature for 4 h to 8 h.

10. A preparation method of the cyclic Gd (III) complex according to claim 1, wherein in formula I, R is selected from the group consisting of $C_2$-$C_4$ alkyl, $—CH_2OH$, $—CH(CH_3)OH$, $—CH_2CH_2OH$, $—CH_2Ph$, $—(CH_2)_2Ph$, $—(CH_2)_3Ph$, $—(CH_2)_3NH_2$, and $—(CH_2)_4Ph$ R' is H, and R" is selected from the group consisting of H, $—CF_3$, $—C(CH_3)_3$, -Ph, $—NO_2$, and —OBn; and the preparation method comprises the following steps:

(1') in a nitrogen atmosphere, mixing a compound with a structure shown in formula E-1, a compound with a structure shown in chiral cyclen, and acetonitrile to allow a first nucleophilic substitution reaction to obtain a compound with a structure shown in formula E-2;

(2') in a nitrogen atmosphere, mixing the compound with a structure shown in formula E-2 obtained in step (1'), acetonitrile, potassium carbonate, and ethyl bromoacetate to allow a second nucleophilic substitution reaction to obtain a compound with a structure shown in formula E-3;

(3') mixing the compound with a structure shown in formula E-3 obtained in step (2'), THF, methanol, and a lithium hydroxide aqueous solution to allow an ester hydrolysis reaction, and subjecting a product of the ester hydrolysis reaction to concentration, dilution, and pH adjustment successively to obtain a compound with a structure shown in formula E-4; and (4') mixing the compound with a structure shown in formula E-4 obtained in step (3'), a gadolinium source, water, and an $M^+$-containing solution to allow a complexation reaction to obtain the cyclic Gd (III) complex, wherein the $M^+$-containing solution in step (4') is a solution of a metal hydroxide or a glucosamine,

E-1

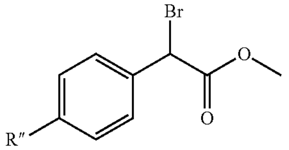

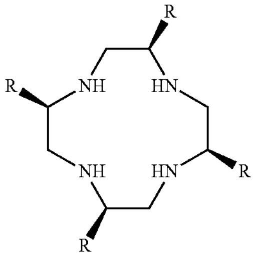

Chiral cyclen

E-2

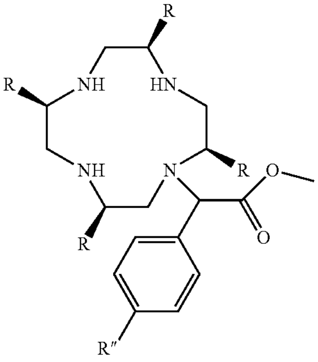

E-3

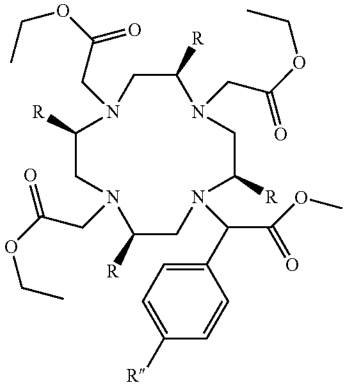

E-4

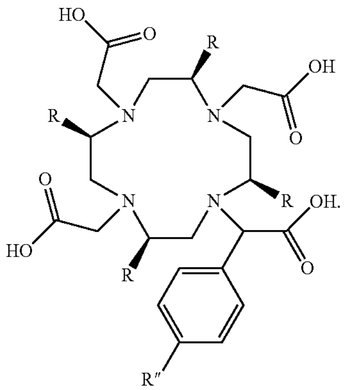

11. The preparation method according to claim 10, wherein R in formula I is selected from the group consisting of $-CH_2CH_3$, $-CH(CH_3)_2$, $-CH(CH_3)OH$, $-CH_2Ph$, and $-(CH_2)_4Ph$.

12. The preparation method according to claim 10, wherein $M^+$ in formula I is selected from the group consisting of $Na^+$, $K^+$, $Li^+$, and a glucosamine cation.

13. The preparation method according to claim 10, wherein the complexation reaction in step (4') is conducted at 90° C. to 110° C. for 5 h to 7 h.

14. The preparation method according to claim 11, wherein the complexation reaction in step (4') is conducted at 90° C. to 110° C. for 5 h to 7 h.

15. The preparation method according to claim 12, wherein the complexation reaction in step (4') is conducted at 90° C. to 110° C. for 5 h to 7 h.

* * * * *